United States Patent [19]
Sliwa et al.

[11] Patent Number: 6,039,701
[45] Date of Patent: Mar. 21, 2000

[54] METHOD AND APPARATUS FOR MONITORING CERVICAL DIAMETER

[75] Inventors: Jack Sliwa, Los Altos; Lee A. Blumenfeld, San Carlos, both of Calif.

[73] Assignee: OB Inovations, Inc., San Carlos, Calif.

[21] Appl. No.: 08/706,575

[22] Filed: Sep. 5, 1996

[51] Int. Cl.[7] ....................................................... A61B 5/00
[52] U.S. Cl. ............................................. 600/588; 600/591
[58] Field of Search ..................................... 128/830, 833, 128/774, 775, 778, 630; 600/304, 587, 588, 591, 300

[56] References Cited

U.S. PATENT DOCUMENTS

| | | | |
|---|---|---|---|
| 2,924,220 | 2/1960 | Micsky | 128/361 |
| 3,731,184 | 5/1973 | Goldberg et al. | 324/34 R |
| 3,744,140 | 7/1973 | Kyrk | 33/179 |
| 3,945,371 | 3/1976 | Adelman . | |
| 4,016,867 | 4/1977 | King et al. . | |
| 4,046,140 | 9/1977 | Born . | |
| 4,141,345 | 2/1979 | Allen et al. . | |
| 4,168,709 | 9/1979 | Bentov . | |
| 4,207,902 | 6/1980 | Krementsov . | |
| 4,245,656 | 1/1981 | Farr et al. . | |
| 4,476,871 | 10/1984 | Hon . | |
| 4,480,642 | 11/1984 | Stoy et al. . | |
| 4,541,439 | 9/1985 | Hon . | |
| 4,611,603 | 9/1986 | Kelso et al. | 128/775 |
| 4,678,893 | 7/1987 | Ruble . | |
| 4,682,609 | 7/1987 | Parsons . | |
| 4,719,925 | 1/1988 | Parsons . | |
| 5,025,787 | 6/1991 | Sutherland et al. . | |
| 5,037,430 | 8/1991 | Hasson . | |
| 5,209,754 | 5/1993 | Ahluwalia . | |
| 5,222,485 | 6/1993 | Jerath . | |
| 5,275,169 | 1/1994 | Afromonwitz et al. . | |
| 5,394,863 | 3/1995 | Sanford et al. . | |
| 5,406,961 | 4/1995 | Artal | 128/778 |
| 5,438,996 | 8/1995 | Kemper et al. . | |
| 5,450,857 | 9/1995 | Garfield et al. . | |
| 5,483,970 | 1/1996 | Rosenberg . | |

OTHER PUBLICATIONS

Anderson, Anne B. "Relationship between length of gestation and cervical dilatation, uterine contractility, and other factors during pregnancy," (1996) Am. J. Obst. & Gynec., p. 1207.

Anderson, H. Frank "Prediction of risk for preterm delivery by ultrasonographic measurement of cervical length," (1990) Am. J. Obstet & Gynecol., p. 859.

Bakke, Trygve, "Cervical consistency in women of fertile age measured with a new mechanical instrument," (1974) Acta Obstet. Gynec. Scand., 53 pp. 293–302.

Bakke, Trygve et al., Chapter 15 of "Dilitation of the uterine cervix" edited by F. Naftolin and P.G. Stubblefield, Raven Press, New York (1980) and entitled "Ultrasonic and mechanical measurement of human cervical consistency".

Bentov, I. et al., Chapter 17 of Dilitation of the uterine cervix edited by F. Naftolin and P.G. Stubblefield, Raven Press, New York (1980) and entitled "Measurement of the tangential force required for dilatation of the human cervix for abortion: Studies with a new mechanical dilator".

(List continued on next page.)

Primary Examiner—Francis Jaworski
Attorney, Agent, or Firm—Townsend and Townsend and Crew LLP

[57] ABSTRACT

An apparatus for measuring cervical diameter comprises a support structure and measurement devices for detecting changes in cervical diameter, either directly or indirectly through changes in the size of the support structure. The support structure may conform to a cervical surface, typically being a peripherally expansible lumen or expansible structure. Alternatively, the support structure may engage the vaginal wall or fornices. Measurement devices may include gages which determine change in sizes of an expansible loop, electronic devices for measuring changes in transmitted or reflected energy, or combinations thereof. The devices are suitable for use on ambulatory patients and in out-patient situations.

70 Claims, 15 Drawing Sheets

OTHER PUBLICATIONS

Bishop, Edward, "Pelvic scoring for elective induction," (1964) Obstetrics and Gynecology, vol. 24, No. 2, p. 266.

Calder, Andrew A., Chapter 22 of "Dilitation of the uterine cervix"; edited by F. Naftolin and P.G. Stubblefield, Raven Press, New York (1980) and entitled Pharmacological management of the unripe cervix in the human.

Calder, Andrew A., "Postaglandins and biological control of cervical function," (1994) Aust. and N.Z. Journal of Obstetrics and Gynaecology, 34: 3, p. 347.

Conrad, John T. et al., Chapter 18 of "Dilatation of the uterine cervix", edited by F. Naftolin and P.G. Stubblefield, Raven Press, New York (1980) and entitled "Anatomic site and stretch modulus in the human cervix".

Daikoku, Norman H. et al., "Diagnosis of prematurity and premature labor," (approx. 1979) source unknown p. 75.

Danforth, D.N. Chapter 1 of "Dilatation of the uterine cervix" edited by F. Naftolin and P.G. Stubblefield, Raven Press, New York 1980 and entitled "Early studies of the anatomy and physiology of the human cervix and implications for the future".

Embrey, M.P., "Cervical Tocodynamometry" (approx 1965) Journal of Obstetrics and Gynaecology, p. 225, issue unknown.

Ferenczy, Alex, Chapter 3 of "Dilatation of the uterine cervix"; edited by F. Naftolin and P.G. Stubblefield, Raven Press, New York (1980) and entitled "The ultrastructure of the human cervix".

Friedman, Emanuel A., "Cervimetry: An objective method for the study of cervical dilatation in labor," (1956) Am. J. Obst. & Gynec., p. 1189.

Friedman, Emanual A., "Electronic cervimeter: A research instrument for the study of cervical dilatation in labor," (1963) Am J. Obst. & Gynec.

Friedman, E.A., Chapter 2 of "Dilatation of the uterine cervix"; edited by F. Naftolin and P.G. Stubblefield, Raven Press, New York (1980) and entitled "Cervical function in human pregnancy and labor".

Hendricks, Charles H. et al., "Normal cervical dilatation pattern in late pregnancy and labor," (1970) Amer. J. Obstet. & Gynec.

Houlton, M.C.C., "Factors associated with preterm labour and changes in the cervix before labour in twin pregnancy," (1982) British Journal of Obstetrics and Gynaecology, vol. 89, p. 190.

Huszar, Gabor B., Chapter 27 of "Dilatation of the uterine cervix"; edited by F. Naftolin and P.G. Stubblefield, Raven Press, New York (1980) and entitled "Relationship between myometrial contractility and cervical ripening in parturition".

Kok, Frans et al., "Ultrasonic measurement of cervical dilation during labor," (1976) Am. J. Obstet. & Gynecol., p. 288, brief communication.

Koob, Thomas, J., Chapter 4 of "Dilatation of the uterine cervix"; edited by F. Naftolin and P.G. Stubblefield, Raven Press, New York (1980) and entitled "Collagen dynamics and extensibility in the female reproductive tract".

Kriewall, Timothy J., "Measuring cervical dilatation in human parturition using the Hall effect," (1977) Medical Instrumentation, vol. 11, No. 1, p. 26.

Lerner, Ulrico, Chapter 21 of "Dilatation of the uterine cervix"; edited by F. Naftolin and P.G. Stubblefield, Raven Press, New York (1980) and entitled "The uterine cervix and the initiation of labor; Action of Estradiol–17 Beta".

McCarthy, Shirley, "Magnetic resonance imaging of the normal female pelvis," (1992) Radiologic Clinics of North America, vol. 30, No. 4, p. 769.

McInnes, D.R., Chapter 12 of "Dilatation and the uterine cervix;" edited by F. Naftolin and P.G. Stubblefield, Raven Press, New York (1980) and entitled "Cervical changes in pregnant women".

Neuman, Michale et al., Chapter 16 "Dilatation of the uterine cervix," edited by F. Naftolin and P.G. Stubblefield, Raven Press, New York (1980) and entitled "Continuous monitoring of cervical dilatation during labor and measurement of cervical compliance in the human".

Nzeh, D.A. "Sonographic assessment of the incompetent cervix in pregnancy", (1992) Int. J. Gynecology Obstetrics, 37: p. 179.

Parikh, Mahendra N. et al., "Internal cervical os during the second half of pregnancy;" (approx. 1960) Journal of Obstetrics and Gynaecology, p. 818.

Phelps, John Y., "Accuracy and intraobserver variability of simulated cervical dilatation measurements;"(1995) Am. J. Obstet. Gynecol., p. 942.

Rice D.A., "A simple model of the human cervix during the first stage of labor;" (1976) J. Biomechanics, vol. 9, p. 153.

Richardson, J.A. et al., "A cervimeter for continuous measurement of cervical dilatation in labour–preliminary results;" (1978) British Journal of Obstetrics and Gynaecology, vol. 85, p. 178.

Schaffner, Fred, "Cervical dilatation in the early third trimester;" (1966) Obstetrics and Gynecology, vol. 27, No. 1, p. 130.

Siener, H., "First stage of labor recorded by cervical tocometry;" (1963) Am. J. Obstet. & Gynec., Jun. 1, p. 303.

Toita, Takafumi, "Prognostic value of cervical size and pelvic lymph node status assessed by computed tomography for patients with uterine cervical cancer treated by radical radiation therapy"; Int. J. Radiation Oncology Biol. Phys., vol. 33, No. 4, p. 843.

Veis, Arthur, Chapter 13, "Dilatation of the uterine cervix"; edited by F. Naftolin and P.G. Stubblefield, Raven Press, New York 1980 and entitled "Cervical dilatation: A proteolytic mechanism for loosening the collagen fiber network".

Wood, Carl et al., "The prediction of premature labor by observation of the cervix and external tocography;" (1965) Am. J. Obstet. & Gynec., p. 396.

Zador, Ivan et al., "Continuous monitoring of cervical dilatation during labour by ultrasonic transit–time measurement," (1976) Medical and Biological Engineering, p. 299.

Zilianti, Mario M.D. et al., "Monitoring the effacement of the uterine cervix by transperineal sonography; a new perspective," (1955) by the American Institute for Ultrasound in Medicine, J. Ultrasound Med. 14:719–724.

Brundin, Keith, "Fiber Optic Sensors: Smart technology for safety;" (1996) Photonics Spectra, p. 106.

Product data sheet, MicroStrain Corp.—StrainLink™ miniature telemetry device.

Product data sheet, SpaceAge Control, Inc.—wire reel–based pots.

Blatt, J. H. "Generation of surface shape from variable resolution video moire contours," (1992) SPIE 1821:304–311.

Guisser, L. et al. "3D measurements and surface properties from a projected grid," (1992) 1821:394–404.

Starks, M. "Stereoscopic imaging technology," (1992) (unpublished manuscript) pp. 1–20.

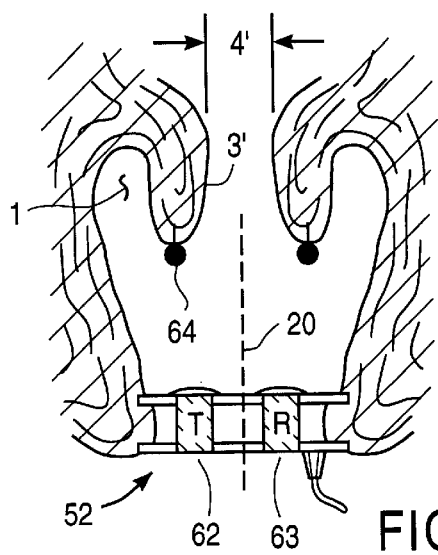
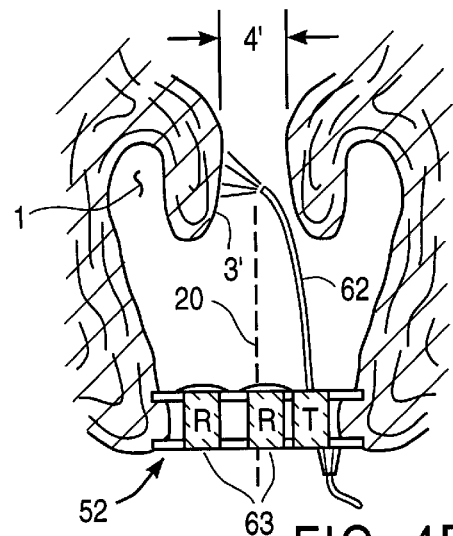
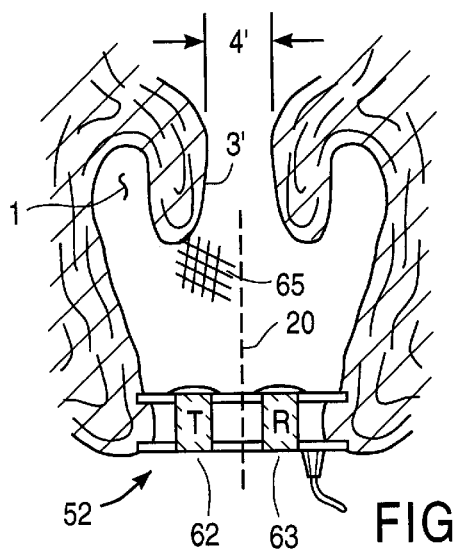
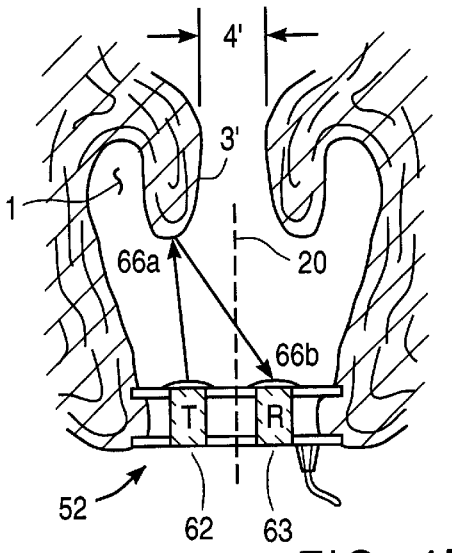
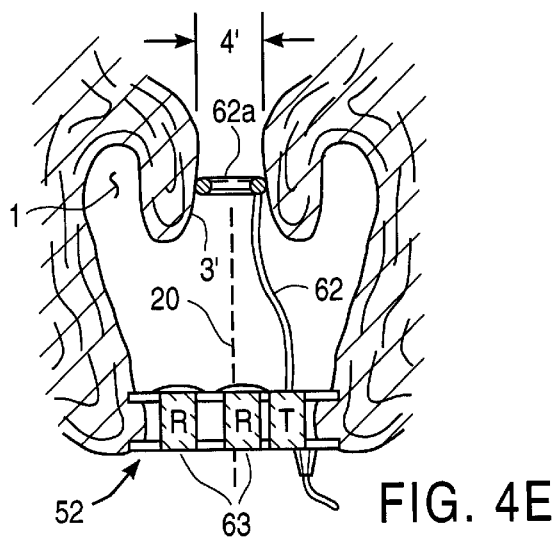
FIG. 4A
FIG. 4B
FIG. 4C
FIG. 4D
FIG. 4E Section Z-Z

METHOD AND APPARATUS FOR MONITORING CERVICAL DIAMETER

BACKGROUND OF THE INVENTION

The present invention relates generally to the field of medical devices and measurements. More particularly, the present invention relates to a method and apparatus for measuring cervical dilation of a patient during pregnancy and labor.

The uterine cervical canal serves as the conduit for the human fetus to exit the uterus and subsequently pass through the vagina during the birthing process. It has long been known that the cervix normally undergoes a series of physical and biochemical changes during the latter portions of pregnancy which enhance the ease and safety of the birthing process for the mother and the infant. For example, in the early stages of labor the tissues of the cervical canal soften and become more pliable, the cervix shortens, and the diameter of the cervical canal begins to increase at its proximal end at the internal os. As labor progresses, the cervical diameter growth propagates to the distal end of the cervical canal to the external os. In the final stages of labor, the external Os dilates allowing for the unobstructed passage of the fetus.

The monitoring of cervical diameter via serial vaginal exams is critically important in labor management. This information regarding the progress of labor is used to diagnose such conditions as dysfunctional or arrested labor and cephalopelvic disproportion, determine the necessity for labor augmentation or cesarean section, indicate when the patient should begin to push the baby out, and determine the appropriateness and timing of administering various anesthetic/analgesic agents, among other things. The vaginal exam is performed by inserting the first and second fingers of a gloved hand into the vagina and up to the cervix. By spreading the two fingers across what is perceived to be the internal diameter of the cervix, an assessment is made, based on experience, about the cervical dilatation in centimeters.

Obstetricians, and other health care providers that are certified to attend obstetrical patients (family practitioners, nurses, midwives), are usually well practiced in the art of manual, digital cervical diameter measurement. An individual practitioner can achieve acceptable repeatability using this method. However, the variation between providers is known to be quite significant due to the subjective nature of the measurements. In addition, such measurements are discrete and must be performed serially to assess labor progress and ascertain whether interventions-are required. It is not an efficient use of a busy obstetrician's time to perform these serial exams, especially when he/she is attending to multiple laboring patients, some percentage of whom may have complications that require most of his/her time.

Despite the use of gloves, vaginal exams also carry with them the risk of causing infections of the fetal membranes (chorioamnionitis), the lining and/or muscle of the uterus (endomyometritis), or of the infant (neonatal sepsis). The risk increases dramatically once the fetal membranes have been ruptured and is related to the number of vaginal exams, among other factors. For this reason, the number of vaginal exams must be kept to a minimum after the membranes have been ruptured.

The measurement of cervical dilatation is also important in patients at risk for preterm labor (prior to 37–38 weeks gestation depending on definition). Neonatal morbidity and mortality increases with the degree of prematurity, so early diagnosis of preterm cervical dilatation and expeditious intervention is critical.

Given the above, it is not surprising that there have been numerous historical attempts to: (A) Provide a more accurate user-independent cervical diameter monitoring device and/or (B) Provide an automatic cervical diameter measuring device. We will review several of these historical attempts below.

Unfortunately, none of these prior-art devices are practical for everyday, inexpensive use for one or more reasons. Consequently, there is currently no commercially available, objective monitoring system for cervical diameter, and the measurement of cervical diameter continues to be performed solely by manual, digital examination.

Reasons for failure of prior-art devices to gain acceptance include:

1) Patient discomfort and cervical tissue trauma due to attachment means.

2) Lack of accuracy due to: (a) imposed cervical tissue distortions, (b) inherently inaccurate sensors, (c) unpredictable sensor reorientation (twisting) errors, (d) flaws in assumptions (ultrasonic cervimeters) and (e) lack of proven and published correlations between other measured cervical-tissue parameters and the actual desired cervical diameter.

3) Blockage of the cervical canal (thus inhibiting other manipulations including the insertion and operation of fetal or intrauterine probes.

4) Complexity of installation.

5) Lack of disposability (thus high cost and a need to resterilize the device).

6) Electrical shock hazards.

7) Unsuitable for ambulatory and/or at-home use.

It would therefore be desirable to provide improved devices and methods for measuring cervical diameter and dilation which overcome at least some of the shortcomings listed above. It would be particularly desirable, at least for patients in danger of premature delivery, if cervical diameter could be measured and monitored at home and, ideally, in an ambulatory manner.

SUMMARY OF THE INVENTION

The present invention provides improved cervimeters and methods for measuring and detecting changes in the size of a patient's cervix and cervical os. Although the following description is directed specifically at performing such measurements in human females, it will be appreciated that the invention can be readily adapted for use in other mammals, although in some cases it might be necessary to change the dimensions and/or geometry of the particular devices which are illustrated herein.

In a first aspect of the present invention, a cervimeter comprises a loop element which is securable to the patient's cervix, where a peripheral dimension of the loop varies directly with changes in the cervical size, e.g. dilation of the cervical os. A gauge is coupled to the loop element for measuring such changes in the loop dimension. The loop element may be directly or indirectly attached to the cervix in several ways.

In a first instance, the loop element is secured to the cervix by a circumferentially expansible race which is attached to or engages a surface of the cervix. For example, the race may engage an interior wall of the cervix and may be secured thereto by anchors. The race may comprise a plurality of individual bearing elements or alternatively may comprise a continuous or semi-continuous structure which is anchored to the cervix.

In a second instance, the circumferentially expansible race will comprise an expansible support structure which conforms to and expands with a surface of the cervix. Typically, the expansible support structure has a surface which conforms to the cervical surface, and the loop element is slidably captured between the support structure surface and the cervical surface, e.g. in an annular channel formed in or near the support structure surface. The expansible support structure will typically include an elastic body, e.g. a foam cylinder which is received in the interior of the cervix or a cup which is received over the exterior of the cervix.

In a second aspect of the present invention, the cervimeter comprises an expansible support structure having a surface which conforms to and expands with the surface, e.g. either an interior surface of the cervix or an exterior surface of the cervix. The cervimeter system further comprises a means for measuring changes in the size of the expansible support, wherein such size changes relate directly to changes in the cervical size. Usually, the support structure comprises an elastic body which mounts within the interior of the cervix or over the exterior of the cervix, e.g. being a foam cylinder or cup as described above.

The measuring means of the second aspect of the present invention can comprise any one of a variety of particular devices. In a first instance, the measurement means can be a loop element generally as described above. In a second instance, the measuring means comprises at least a first measurement node and a second measurement node, where the nodes are detectable in any one of a variety of ways by electronic, optical, ultrasonic, or other signals. In a first exemplary embodiment, the first measurement node comprises a transmitter and the second measurement node comprises the receiver, and circuitry, is coupled to the transmitter and the receiver for determining the distance between said nodes. In a second exemplary embodiment, both of the first and second measurement nodes comprise at least one receiver, and an external transmitter is provided together with circuitry for determining the distance between the node/receivers when the receivers are excited by the transmitter.

In a third aspect of the present invention, the cervimeter comprises a support structure which engages and adheres to the cervix or vaginal wall proximate the cervix, but generally does not conform to changes in the cervical diameter. The support carries means for measuring changes in a cervical dimension. The support structure can comprise an expansible support structure, such as an elastic body as described above, which conforms to the vaginal wall in the region of the cervix (but which does not expand and contract with changes in the size of the cervical os). Alternatively, the structure can comprise a ring which is mountable within the vaginal fornices. The support means would also comprise spring(s) having at least two elements, each of which engage an inner peripheral surface of the cervix. The spring elements will thus be able to move radially inwardly and outwardly as the cervix expands or contracts. In any of these instances, the measuring means can comprise a variety of devices. For example, the measuring means may comprise at least two radially deployable wires, each having a distal end which is securable to a peripheral location on the cervix. The gauge is coupled to the wires for measuring movement of said wires as an indication of changes in cervical size. Alternatively, the measuring means can comprise an expansible coil which is insertible into a cervical os and which uncoils as the os dilates. The gauge, such as a force measuring element, can be coupled to the coil for measuring size changes in the cervical os. In the case of the spring support, measurement nodes as described generally above may be mounted on the spring elements to provide for measurement of the cervical os.

In a fourth aspect of the present invention, a cervimeter comprises a support structure which is securable within a vaginal cavity, typically within the entry of the vagina. The support structure carries a transmitter for directing an energy flux or energy field onto the cervix, wherein the energy flux or field is reflected or emitted from a cervical surface in a pattern which depends on a cervical dimension. A receiver on the support detects patterns of emitted or reflected energy, and the cervical dimension can be determined from such detected patterns. The energy transmitted may be optical, wherein the cervimeter may comprise two or more reflectors which are securable to cervical surfaces. In such cases, the receiver may comprise a charge-coupled device (CCD). In other cases, the transmitter may comprise an optical fiber which extends from the support structure toward the cervix, and where optical energy is directed through the optical fiber onto the cervical surface. In still other cases, the transmitter may project a particular pattern of light over the cervical surface, where the transmitter may comprise an optical laser. Apparent distortions in the projected light patterns(s) may be used to determine the dimensions and/or shape of the cervix.

The present invention still further provides methods for detecting changes in the size of a cervix. In the first aspect of the methods of the present invention, the conformable structure as secured to a surface of the cervix, and the structure has a periphery which expands and contracts together with expansion and contraction of the cervix. The size changes are thus detected by measuring expansion and contraction of the periphery of the conformable structure. The conformable structure may comprise any of the devices and apparatus described above, such as a loop element wherein the measurement step comprises measuring uptake and release of the loop element. Alternatively, the conformable structure include a plurality of measurement nodes about its periphery, wherein the measuring step comprises detecting the relative position of at least one pair of the measurement nodes as an indication of a change in cervical dimension. The measurement nodes may be any of the particular devices described above.

In a second aspect of a method of the present invention, an energy flux or field is transmitted from a location in the vaginal opening or cavity to the cervix. Reflected or emitted energy from the cervix is detected, and changes in cervical size determined based on detected patterns of energy. The energy and measurement techniques may be any of those generally set forth above in connection with the apparatus of the present invention.

BRIEF DESCRIPTION OF THE DRAWINGS

In FIG. 3B, both of the sensors sense a positioning energy field which is transmitted from other than one of the two sensor locations. The differential positions of the sensors are related to the cervical Os diameter.

FIGS. 3C and 3D illustrate two alternative embodiments of an in-plane radially expanding cervimeter wherein FIG. 3C shows a radially extracting-wire cervimeter and FIG. 3D shows a radially unrollable, uncoilable, unwrappable or unbendable coil spring cervimeter. The spring(s) may undergo combined radial and circumferential motions.

FIGS. 4A, 4B, 4C, 4D, and 4E illustrate five embodiments of the orthogonal form of the cervimeter. FIG. 4A utilizes optical reflectors mounted on the cervical tissue and imaging of the reflections therefrom. FIG. 4B utilizes selective illumination of the cervical interior and subsequent imaging of the lighted interior structures. FIG. 4C utilizes a projected graticule or other structured light image whose apparent projected distortions and size changes allow for the computation of dilation and surface topography. FIG. 4D utilizes optical triangulation, preferably using a laser. FIG. 4E utilizes an illuminated fiber optic fiber which conforms to at least a portion of the surface to be measured and subsequent imaging of the glowing segment(s) of fiber to determine cervical diameter.

FIG. 5A shows a nitinol spring structure having an expansive loop region which anchors in or near the vaginal cavity wall. FIG. 5B shows a nitinol spring structure with expansive cantilevered arms situated on or near the vaginal cavity wall.

DESCRIPTION OF THE SPECIFIC EMBODIMENTS

The invention herein takes one of two general forms. The first form is referred to as in-plane cervimetry wherein the cervimeter of the invention operates in one or more planes in (or parallel to) the plane in which the diameter to be measured resides. We describe two types of in-plane cervimetry: circumferential and radial. The two types may be used in unison or individually. In contrast to the variety of referenced examples from the prior art, these in-plane solutions can offer direct cervical dimension sensing, undistorted average diameter measurements, minimal or no tissue trauma, disposability, minimization or elimination of shock hazards, easy installation, optional ambulatory operation, and optional uterine access. Also, prior-art concerns about the unpredictable twisting movement (or angulation) of paired sensors and the resultant errors therefrom are largely avoided, as is any need to make assumptions about tissue properties.

The second form of the invention is referred to as orthogonal plane cervimetry. These orthogonal-plane cervimeters achieve their direct measurements in at least one plane generally orthogonal to the outer Os (like prior-art instrumented forcep devices); however, prior-art problems of patient irritation, cervical tissue trauma, difficulty of installation, lack of ambulatory freedom and uterine access blockage are overcome by avoiding the need to attach any bulky articles to the cervical tissues. Anything attached to or coupled to the dilating cervical tissue is extremely light in mass and is extremely compact. Several of the orthogonal cervimeters of the invention are also disposable. All have minimal or no shock hazards.

In explaining the design and operation of the two forms of the invention and the embodiments thereof, we will utilize a number of descriptive figures wherein like item numbers refer to like items from figure to figure.

Figure 1A:
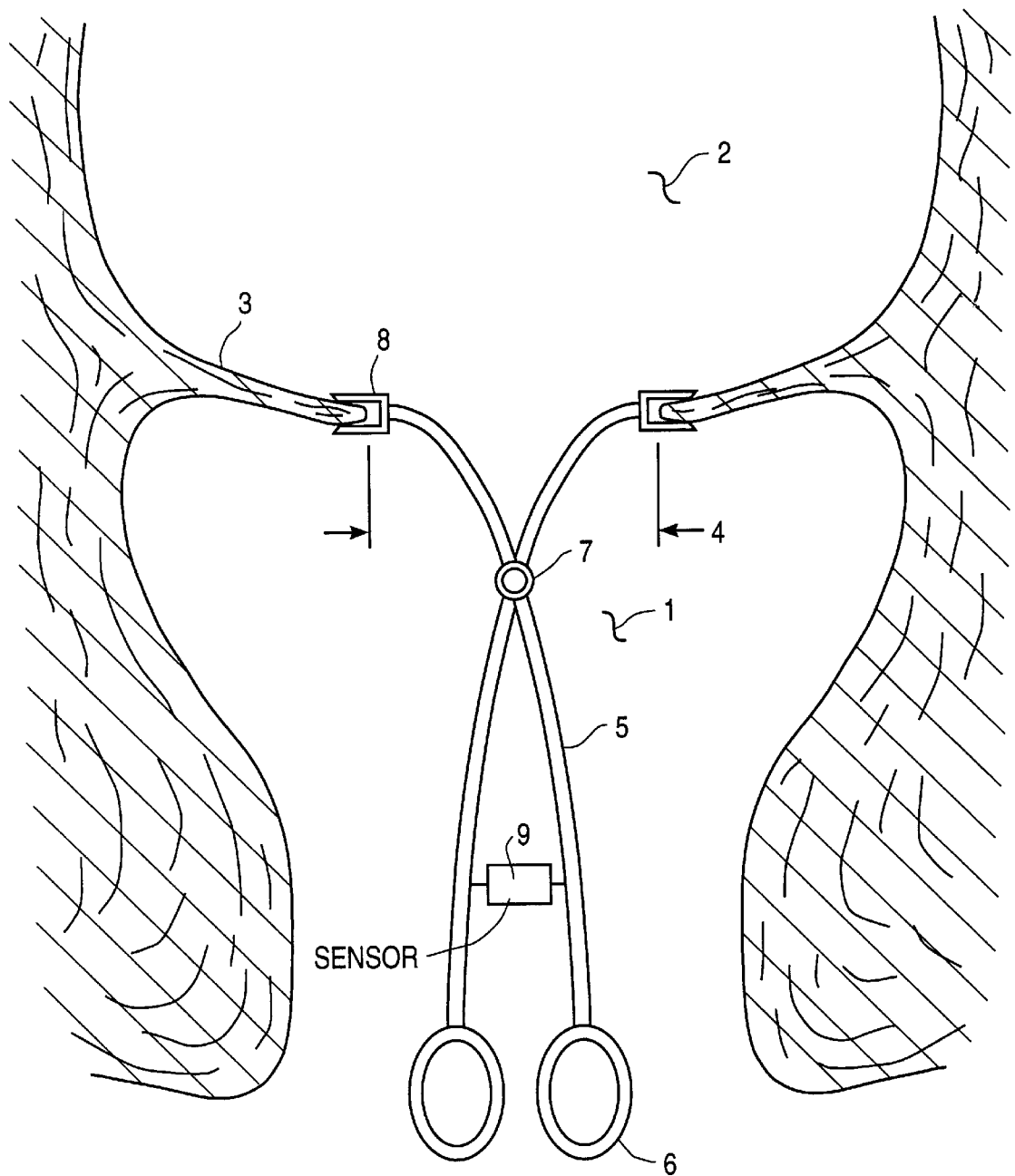
FIG. 1A illustrates a prior-art manual forceps-based cervimeter.

Beginning now with FIG. 1A we show a prior-art scissors or forceps-style cervimeter 5 as referenced above. A vaginal cavity 1 is shown leading to a uterus 2 with a dilated circumferential cervical lip 3 separating the two. It will be appreciated that a large dilatation diameter 4 is depicted and only a thin dilating lip 3 of the cervix remains in the path of the fetus (not shown) which is to descend from uterus 2 above at birth. A scissors or forceps-style cervimeter 5 is shown gripping cervical lips 3 with cervimeter clamps (or barbs) 8. Cervimeter 5 has a pivot axis 7, an integrated sensor 9 capable of providing an electronic readout relating to the degree of dilatation 4 (and thus opening of the forceps) and finger holes 6. The sensor 9 wires are not shown. It will be noted that cervimeter 5 interferes with access to vagina 1 and uterus 2. Sensor 9, as seen in the prior-art, may be any kind of displacement or rotation sensor such as a strain gauge or a rotary potentiometer. It will also be appreciated that cervimeter 5 can bounce around and irritate the patient during ambulatory motion. Finally, one will note that the mass of cervimeter 5 is hung by only two suspension points at clamps (or barbs) 8 and may, under some conditions of patient motion and orientation, significantly distort the diameter reading due to the very limited gripping area and the weight of the cervimeter 5, if not tear the tissue outright.

Cervical tissue tearing has been seen at clamps 8 for these reasons. Such tearing may take place during blind installation or during wear. Unintended pulling on the wires (not shown) could also easily tear tissue at clamps 8. This type of device 5 really only works with a prone stationary patient, and even then with all of the stated limitations. Practically speaking it is a research device.

Figure 1B:
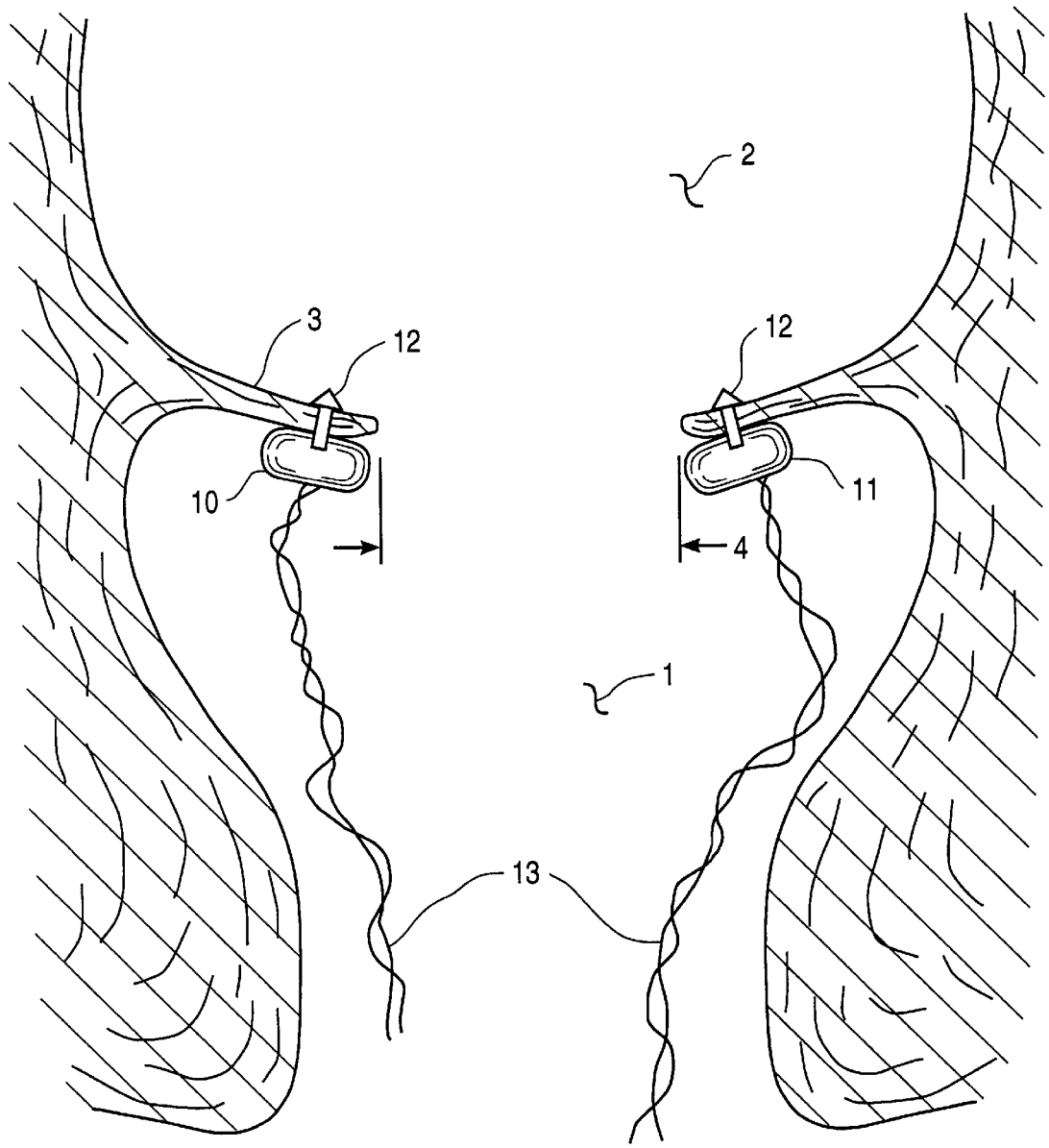
FIG. 1B illustrates a prior-art ultrasonic-based cervimeter.

Moving now to FIG. 1B, we show a prior-art ultrasonic cervimeter of the general known type referenced above several times. Again, a vaginal cavity 1 and uterus 2 are shown separated by a dilated cervical lip 3 whose dilatation diameter is indicated by dimension 4. Mounted on the left side of cervical lip 3 is an ultrasonic transmitter 10 pinned to lip 3 by a single-point barb 12 as is common in the prior-art. On the opposite side, or right-hand side of FIG. 1B there is shown the corresponding receiving ultrasonic sensor 11 pinned to the (opposite) cervical lip 3 by a similar barb 12. Shown emanating from both ultrasonic transmitter 10 and receiver 11 are interconnection wires of the type 13. The wires are shown randomly disposed in the vaginal cavity to emphasize that the wires 13 are unmanaged, can interfere with access to the uterus and can move and cause irritation. A voltage pulse of significant magnitude (usually tens of volts) is repeatedly sent to transmitter 10. This presents some danger to the patient and requires exceedingly careful management of the insulation on wires 13 and of any possible electrical leakage or breakdown path from transmitter 10 or wires 13. The barbs 12, as discussed previously, are single point barbs which unavoidably allow for twisting and tilting motions of the transmitter 10 and receiver 11 about their attachment points. The barbs 12 also, as stated in the prior-art itself, do not provide good acoustic coupling to the cervical tissue 3 and such acoustic coupling must depend on the status and disposition of mucus (not shown). We have above outlined with reference to the prior-art the variabilities of the acoustic path and of acoustic propagation velocity for the acoustic signal to travel from transmitter 10 to receiver 11. The space between 10 and 11, as defined by the most direct straight-line path such as diameter 4, consists of cervical tissue 3 and largely at least one of air, mucus or the presenting part depending on the state of cervical dilatation and the station of the presenting part of the child. There is no easy way to acoustically compensate for these changing material proportions as a function of dilatation, mucus pullback and fetal descent. There is also no easy way to tell whether the acoustic signal actually passed circumferentially around the cervical rim 3 in these cases. Granted one will always get an acoustic signal transmitted from transmitter 10 to be received by receiver 11, but its path is highly variable, possibly multipath in nature, and passes through varying amounts of different materials each with its own variable velocity. The incorrect assumptions of these prior-art ultrasonic approaches are the assumed straight line path and the assumed fixed propagation velocities. Neither is even close to the actual case. The path of acoustic propagation is highly variable from patient to patient, from pregnancy to pregnancy and is inherently unpredictable. Our FIG. 1B shows air space within dilated cervical diameter 4 to emphasize this point; however, it will be obvious from the numerous references that, depending on the station or position of the fetus and the state of cervical dilatation, the cervical canal (which evolves into a cervical lip opening as shown in FIGS. 1A and 1B in late labor) may be filled with air, mucus or with the child's presenting part.

Figure 2:
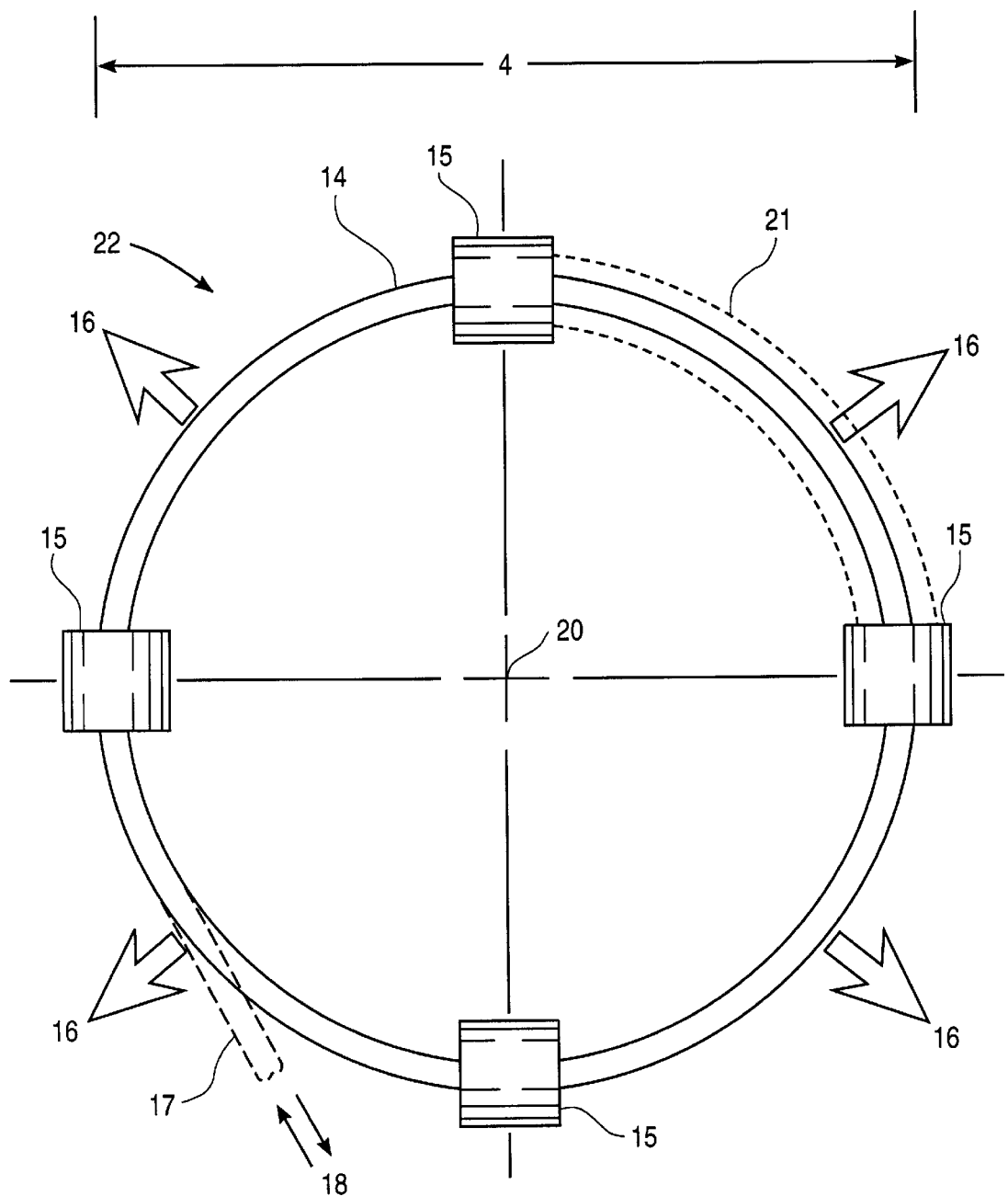
FIGS. 2 and 2E illustrate a cervimeter device of a first "in-plane form" utilizing a circumferentially expanding loop or hoop to track the diameter of the dilating os.

We will now discuss the invention herein. Moving to FIGS. 2 and 2E, there is schematically shown a circumferentially expanding in-plane loop or hoop cervimeter 22 of the first form of this invention. Only the right side of the tissue structures are depicted for simplicity (FIG. 2E). Familiar features from earlier figures can be seen such as vaginal cavity 1, uterus 2, cervical lip 3 and dilated cervical diameter 4. Also shown are schematic front and top views of a wire ring-shaped, circumferentially expanding cervimeter 22 of this invention having a central axis 20 (FIGS. 2E and 2, respectively). A wire loop 14 is generally circular in shape as shown. Although described as "wire," the loop could be in any elongate circularized form, such as ribbon, tube, filament, and the like. The loop will be composed of an elastic material, usually a metal, preferably a superelastic metal, such as nickel-titanium alloy (nitinol), it could also be an elastic, bendable organic polymer. The wire loop 14 is arranged to allow for an increasing circumferential length as it increases its radius (or diameter) as indicated by arrows 16 to follow and track the dilating diameter 4. Extra wire 17 is shown schematically being fed to the expandable loop 14. Arrows 18 demonstrate the optional ability of the wire feed 17 to not only accommodate gradually increasing dilatation diameter 4 but to also accommodate momentary decreases in dilatation diameter 4 as are known to occur during labor. A number of anchors or gripping anchors 15 are shown through which wire loop 14 is guided. The purpose of anchors 15 is to form a "race" for receiving the loop 14 and act as guidance bearings to control the location of loop 14 and to insure that the dilatation is physically tracked by the loop 14. Four such anchors 15 are shown. In the top view one may see that anchor 15 optionally has barbs 12 for tissue attachment. One may also see that the sectioned anchor 15 in the middle of the figure has tapered (or radiused) interior surfaces 19 which allow for some degree of twist of the anchor 15 and/or wire 14 relative to each other without binding. The bearing action of anchor 15 occurs as the loop 14 expands, and it is naturally necessary for the loop to slide within the anchors 15 which are attached to the tissue 3. Thus, the anchors 15 themselves generally move in a radial manner with the increasing dilatation 4, whereas a given point on the wire 14 moves in both a radial and generally circumferential manner. The anchors 15, in addition to allowing for circumferential sliding of wire 14, also insure that the wire loop 14 grows with and tracks the shape of the dilating cervical tissue 3.

Other important generic aspects to note from FIGS. 2 and 2E are as follows:

1) The wire 14 surfaces and anchor 15 bearing surfaces, such as 19, are arranged to slide easily against each other as achieved through one or more of surface finishes, lubricants and/or material selection for example. Thus, the wire 14 and/or anchors 15/19 might be coated, at least at their contact areas, with a fluoropolymer or other slippery and biocompatable coating such as polyimide, polyethylene or PTFE (polytetrafluoroethylene).

2) Any means of tissue attachment may be utilized by anchors 15 and the invention is not limited to single penetrating points or barbs 12. For example, the anchors could have two or more penetrating features per anchor 15, barb-less surface tissue adhesive means, suction vacuum-clamping means, dense arrays of microbarbs, or the like. As an alternative to discrete anchors 15, (to be seen in a later embodiment), the wire loop 14 may be urged against either an inside diameter or outside diameter of a cervical structure using an expandable support structure (shown in a later figure) or using the springiness of coiled wire 14 itself. The anchors 15 might also be used in combination with an expandable support member.

3) Any number of anchors 15 may be used and the anchors 15 may themselves be compliant in at least a circumferential direction. The anchor(s) 15 may even be continuous (shown as broken line structure 21 in FIG. 2 connected in the form of one or more circumferentially expandable polymeric or metallic (e.g. nitinol) tubular or spring-like entities with integrated attachment means such as an adhesive or a plurality of microbarbs. In this case, the anchor(s) may take the form of a continuous, circumferentially expandable elastic sleeve.

4) One may employ separate anchor-spacing means which insure proper circumferential location of anchors 15 during cervimeter 22 handling and through the patient attachment step. For example, one could have circumferentially compressible polymeric tubular material or even circumferential springs which are wrapped or sleeved coaxially with the wire 14 and which act to push the anchors 15 apart circumferentially and keep them properly spaced (typically equally spaced-apart) at least until device 22 is attached or mounted to the patient. Such a spacing means may also be depicted by phantom lines 21 in the cervimeter 22 front view of FIG. 2. It would naturally be utilized over most of the circumference if used at all. Such a sleeve material 21 may also be used to achieve acceptable tissue biocompatability and may also act to promote the needed sliding of the wire 14 relative to underlying tissue 3. Sleeve material 21 may also at least partially encapsulate anchors 15, assuming the anchors 15 are necessary. Sleeve material 21 may also provide a mechanical biasing force (i.e., may itself be radially expandable or contractible) to cause the loop or hoop 14 to grow (or even shrink) or extract (or eject) incremental source wire 17.

5) If wire loop 14 were placed in an inside body diameter (such as a position in the cervical canal to measure a cervical interior diameter) and was radially outwardly mechanically biased, as by an expanding support structure (seen in a later figure), by its own springiness, by an inflating balloon (not shown) or by a circumferentially expansive sleeve 21 as just discussed, then wire loop(s) 14, for many anatomical situations, would be able to be held in place and track a diameter 4 without anchors 15. The same applies to a cervical outer diameter measurement and inward biasing of a loop 14. The early stages of cervical canal dilatation wherein such a clearly defined tubular inside (and outside) diameter of the cervix exists could at least support such an anchorless device. The cervical diameter 4 as shown in FIGS. 1A, 1B, and 2E is seen in the late stages of labor wherein all that remains of the cervical tubular canal is a thin, radially dilating diaphragm or membrane lip 3 as shown. With this structure, we have shown the "anchor" attachment features 15/12 in FIG. 2E. We have also described alternative embodiments of anchors 15 looking more like circumferentially expanding elastic material 21 or circumferential sleeve-springs 21 capable of tissue 3 attachment via an integral attachment means such as an adhesive.

6) FIGS. 2 and 2E show wire 17 being fed into loop 14. One may measure the amount, or more correctly the linear length, of such wire as it is fed into the expanding loop 14. Since circumference is Pi times the diameter (C=πD), the loop diameter change can be determined from the circumference change (which equals the incremental wire feed amount) divided by Pi. One might use, for example, a linear displacement sensor (not shown here) through which the wire 17 passes to achieve this purpose.

7) The circumferentially expanding loop cervimeter 22 of FIGS. 2 and 2E may utilize any convenient "wire" for loop 14. For example, one could use superelastic nitinol alloy wire as is frequently utilized in catheters and guidewires. Nitinol (e.g. Tinel™) materials are available, for example, from Raychem Corp. of Redwood City, Calif. These are extremely elastic and kink resistant. One could also utilize optical fiber, thus providing a convenient optical path for any desirable optical connections. "Wire" 14 may be solid or hollow in cross-section and may itself be a braided, wound, wrapped or otherwise multifilament structure such as a finely wrapped or spun microcable. Wire 14 may also take on a chain-like (eg. linked) or belt (eg. tape) structure wherein it may consist of a series of links such as chain links or joined elements (e.g. like a lamp chain) or alternatively of a solid or linked nonround cross-section belt such as a nitinol metal tape of rectangular cross-section. The only limit placed on "wire" 14 is that it can be held in the form of a loop of changing diameter. Any of these "wire" 14 styles may or may not utilize coatings for lubricity (easy sliding against juxtaposed surfaces without catching), for biocompatability, for electrical insulation or any other purpose.

8) The central portion of the cervimeter 22 in the region of central axis 20 depicted in FIGS. 2 and 2E may optionally allow for access to the fetus and/or uterus for unrelated purposes such as to perform an amniotomy (rupturing the fetal membranes) using an amniotomy hook, to install various sensors or catheters (e.g. intrauterine pressure transducer, fetal scalp electrode, oxygen sensor, thermocouple, amniotic fluid sampling catheter), and to perform fetal scalp blood pH sampling without necessarily removing the cervimeter device 22.

9) The portion of cervimeter 22 depicted in FIGS. 2 and 2E may be disposable. Connection may be made to the nondisposable portion of the cervimeter system (not shown in FIGS. 2 and 2E), which itself may include a wire incrementation measuring means, a recording means, a display means for reporting the diameter, an alarm means and possibly a telemetry means, etc.

10) The method of feeding the wire 17 into the loop 14 may involve, for example, a special anchor, fitting or guide (not shown) which has ports or guiding surfaces for routing the new wire 17 into the loop 14 in a manner such that the total amount of wire in the loop 14 is always a known quantity capable of being reported and/or recorded as necessary. With or without such a wirefeed fitting the fed wire 17 is directed into the growing loop 14 in a manner such that the tracked diameter can be determined. It is to be emphasized that the tracked diameter may be diameter 4 (FIGS. 1A, 1B, 2E) or any other internal or external cervically-related dimension of medical interest or dimension having a predictable or known correlation to a diameter of medical interest. In this manner, measurement of dimensions known to track or be related to the dimension of interest (e.g. diameter 4) may be utilized. Within the scope of the invention is the sensing of the growth of the outer cervical diameter (O.D.) in proximity to the external os, not from in the os itself but from within the vagina (to be seen in FIG. 2D). In such an application one typically wants to report any significant cervical changes indicating premature labor has begun.

11) From a mechanical point of view, in order to know the instantaneous size of the wire loop 14 of cervimeter device 22 and the amount of wire in it, one must be sure that incremental amounts of wire 17 fed to the loop 14 are all ending up in loop 14 and not in a tangled pile elsewhere. If one places the device which measures the wire feeding increments outside the body or otherwise remote from the loop 14, one must assure that the actual amount of wire making it into the growing loop 14 is accurately known. As an example, in a poor design one might have incremented wire 17 bunching up in the vagina and not being added to the loop 14 but still (incorrectly) being reported as a diameter 4 increase. An excellent solution to this challenge can be found in catheter technology. Specifically, if the feedwire 17 between the loop 14 and the external wire-increment measuring device (not shown in this figure) is fed through a slightly larger hollow tubular catheter like guidetube which is axially rigid (not shown in this figure), then one knows that any wire entering that guidetube from the wire-increment measuring device is actually fed into the loop 14. This is because such a guidetube or hollow tubular catheter would be fixedly attached to the wire increment measuring device as well as, for example, to one of the anchors 15 used as a wire feed inlet to cervimeter 22. Thus, due to this tubular container for the wire 17, a flexible container which cannot appreciably change length despite bending due to body movement, one knows that any wire fed in one end makes it into loop 14 of device 22 at the far end.

12) One may store the "feedwire" 17 within the growing loop 14 itself. For example, one could have loop 14 consist of several windings or wraps (turns) of wire which circumferentially uncoil as the cervical diameter grows, such that as time goes on there are a decreasing number of turns in the loop 14 but the same approximate total length of wire having a larger (uncoiled) diameter. This type of design would not necessarily require an external feedwire 17 but would require a means of detecting the amount of such unwrapping or uncoiling to deduce the uncoiled diameter. One could fit portions of such a wire with strain gauges, for example, which detect the curvature (and therefore the diameter) of the wire such that the diameter can be determined from one or more such readings.

In such a strain-gauge, curvature-detection approach one might further only utilize wire segments (separate segments of a circle) having such strain gauges such that the wire segments may both unbend and move radially with increasing diameter but not necessarily move in any sliding (unwinding) circumferential manner as for the prior continuous wires herein. In fact, for this design the wire segments may be provided in the form of any bend-sensing strain gauges of circular segment form which can be held against the tissue in a manner wherein their curvature can be detected accurately. The strain gauges can be held in place against the tissue using an expanding backer having contact with most or all of the tissue diameter or dimension of interest.

13) From the laws of electricity and electromagnetics it will be realized that the loop (or multiturn loop) 14 is an electromagnetic coil. That is to say that loop(s) 14 will create a magnetic field if current is urged along the length (circumference(s) of the loop) of wire 14 and that if a magnetic field is imposed onto the vicinity of loop(s) 14 that reactive voltages will be urged or created in the wire 14. These principles may alternatively be utilized to measure the size of loop 14 rather than using the physical measuring of wire increments as discussed earlier. For example, if a small electromagnetic excitation coil were placed in proximity to loop 14 and excited, a voltage could be detected along the length of wire loop 14 which is directly related both to the number of remaining instantaneous turns (loops) and to the instantaneous diameter of loop(s) 14. The converse may also apply in that if a small current or current pulse is urged along the length (circumference) of loop(s) 14 that a magnetic field may be sensed near the wire which is related to the number of turns and the diameter. Obviously for a multiturn loop 14 one may electrically isolate one turn from another as by insulating the wire 14 along its length. The advantageous use of any such known and generic electromagnetic properties of coils for deducing the diameter of a loop(s) 14 is expressly also incorporated in the invention. The basic advantage of such approaches is that an external feedwire of the type 17 may be avoided along with its inherent feeding and incrementing means. Such a solution would utilize either measurements of the electrical/magnetic properties of the loop(s) itself, optionally using a separate voltage or magnetic field imposition or measurement device coupled to the loop(s).

14) Of alternative possible use is an approach wherein the "wire" material is utilized as an emitter (or detector) in combination with a separate detector (or emitter), say in the center of the loop 14. As an example the "wire" may be a glowing (optically leaky) illuminated optical fiber and a photodetector at or near the center of loop 14 (in the region of 20) senses the integrated optical output of the fiber, the sensed output decreasing as the loop moves further and further away. In yet another example the wire 14 may itself be magnetized and a magnetic sensor (such as a Hall sensor or magnetoresistive sensor) in the region of 20 senses the decreasing magnetic field at 20 as the loop 14 grows. The reader will soon realize that these are special extreme cases of the embodiment to be described in our later FIG. 3.

15) For FIGS. 2 and 2E and any later figure showing barbs 12 or other penetrating attachment means 12 one familiar with the anatomy of the female reproductive organs will be well-aware to avoid utilizing such barbs 12 in the vicinity of the uterine arteries (not shown) which reside in the 3 o'clock and 9 o'clock positions.

Figure 2A:
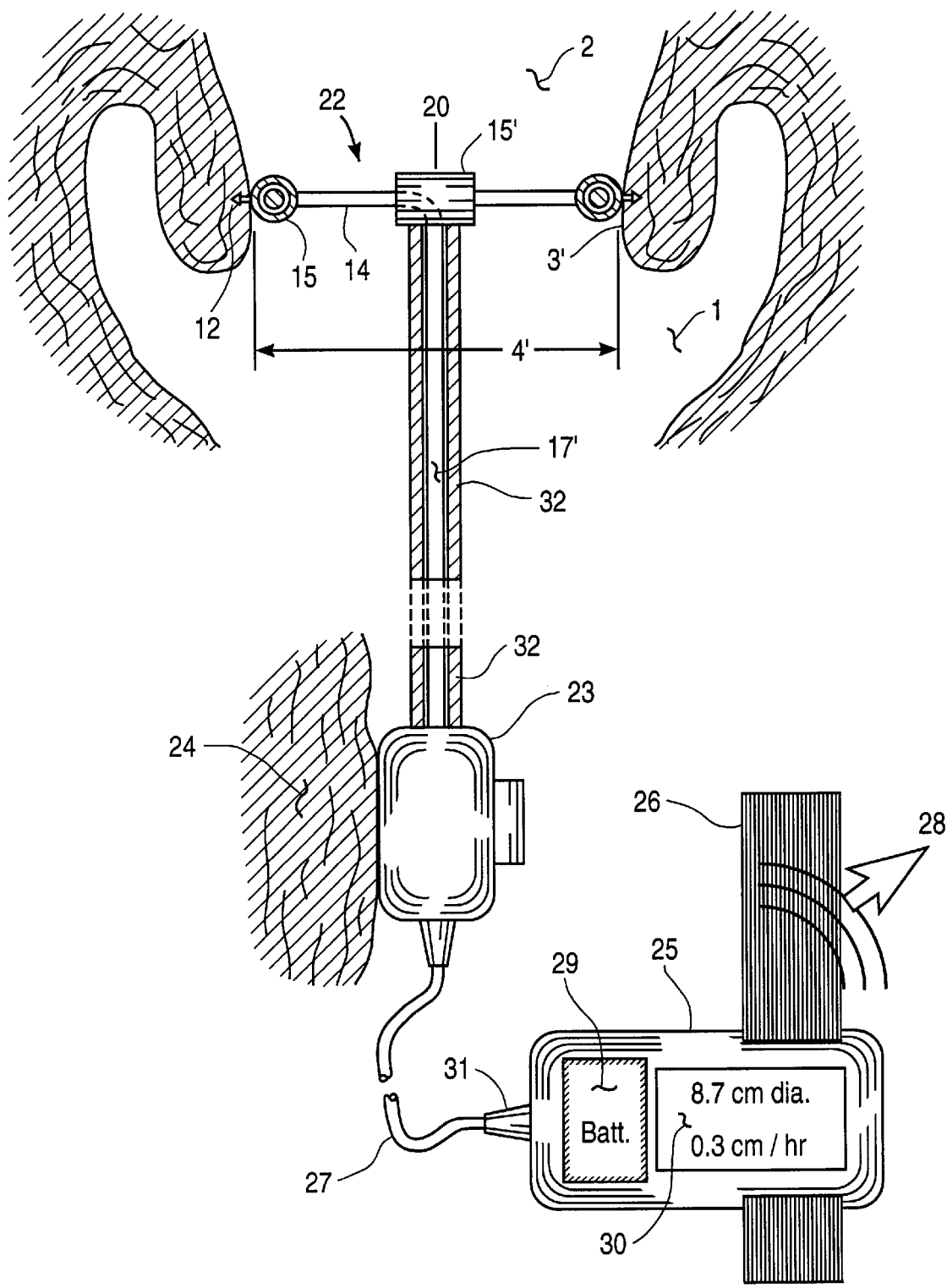
FIG. 2A illustrates a cervimeter system employing the loop cervimeter device of FIGS. 2 and 2E and including electronic monitoring and a readout device.
Figure 2B:
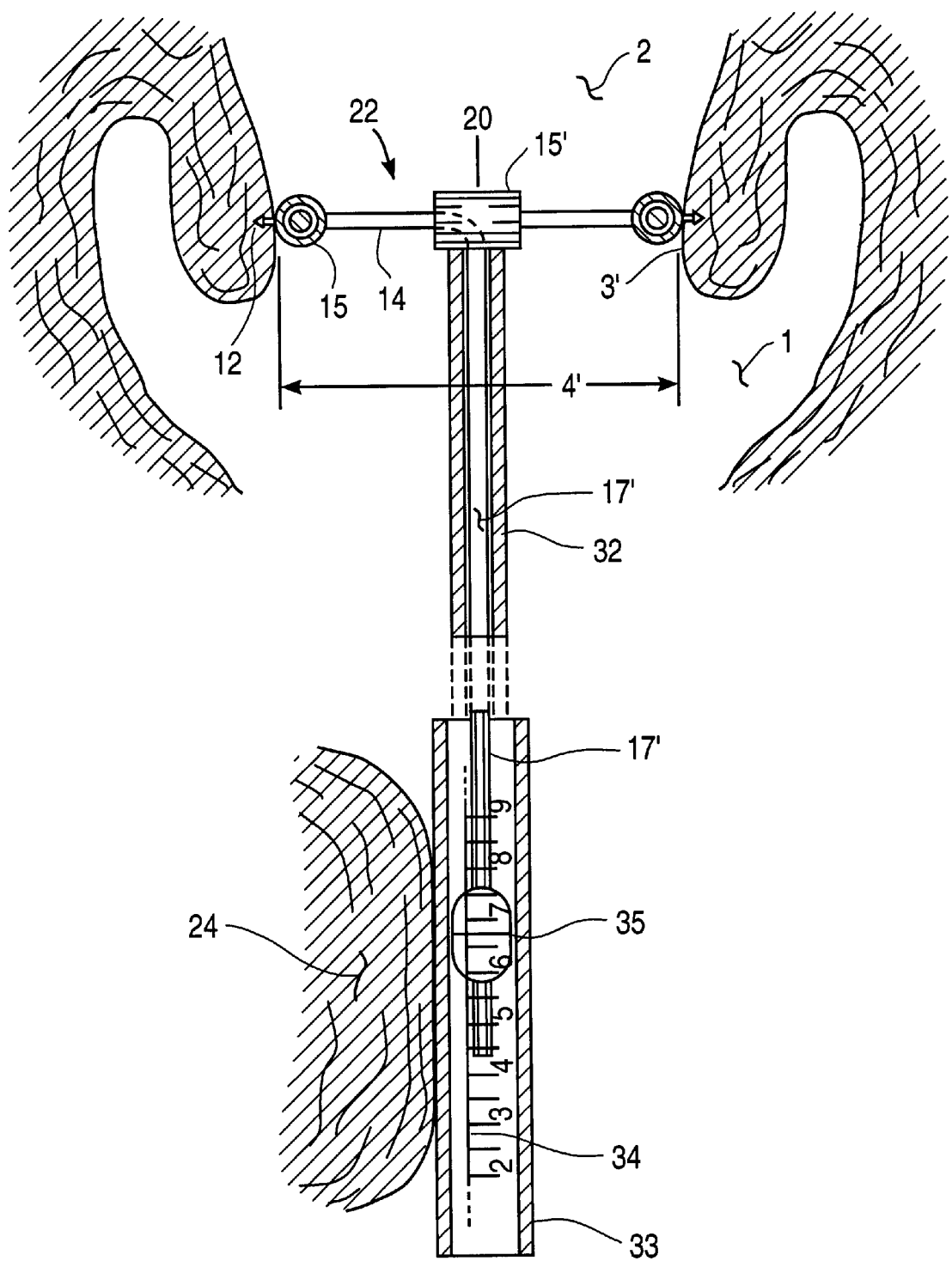
FIG. 2B illustrates a cervimeter system also employing the loop cervimeter device of FIGS. 2 and 2E and including an alternative simple nonelectronic readout means.
Figure 2C:
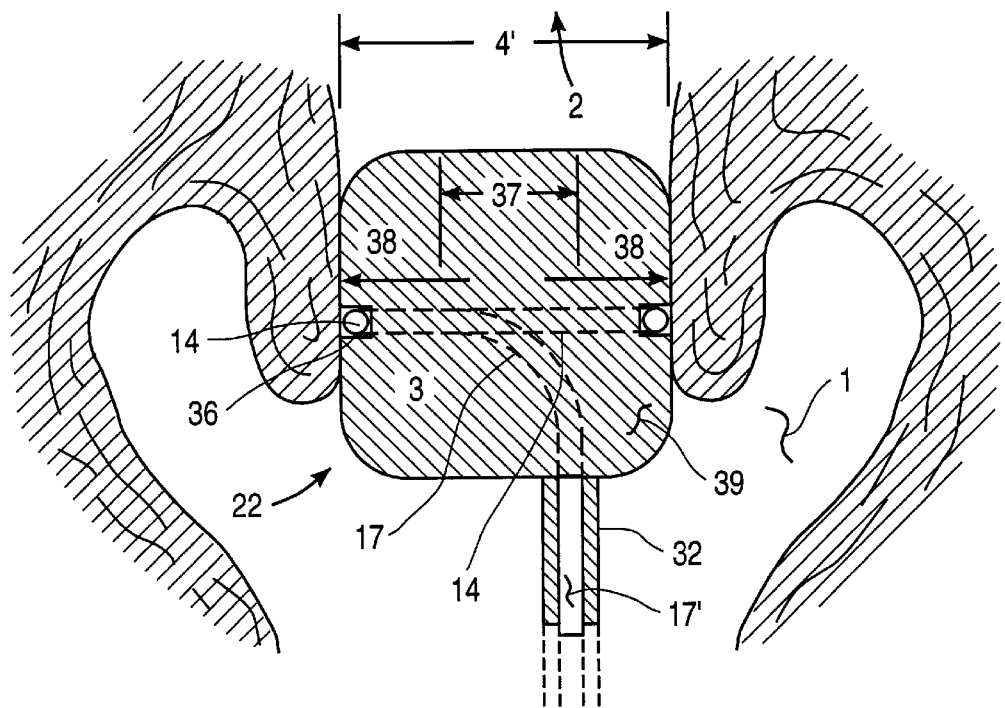
FIGS. 2C and 2D illustrate two cervimeter systems also employing the loop device of the type seen in FIGS. 2 and 2E. The system in FIG. 2C resides mainly in the interior of the cervix and utilizes an expandable structure to assure adjacency of the loop to the internal diameter of the cervical canal. The system of FIG. 2D resides mainly on the exterior of the cervix in the vagina and also utilizes an expandable structure to assure adjacency of the loop to the diameter (interior or exterior) being measured.
Figure 2D:
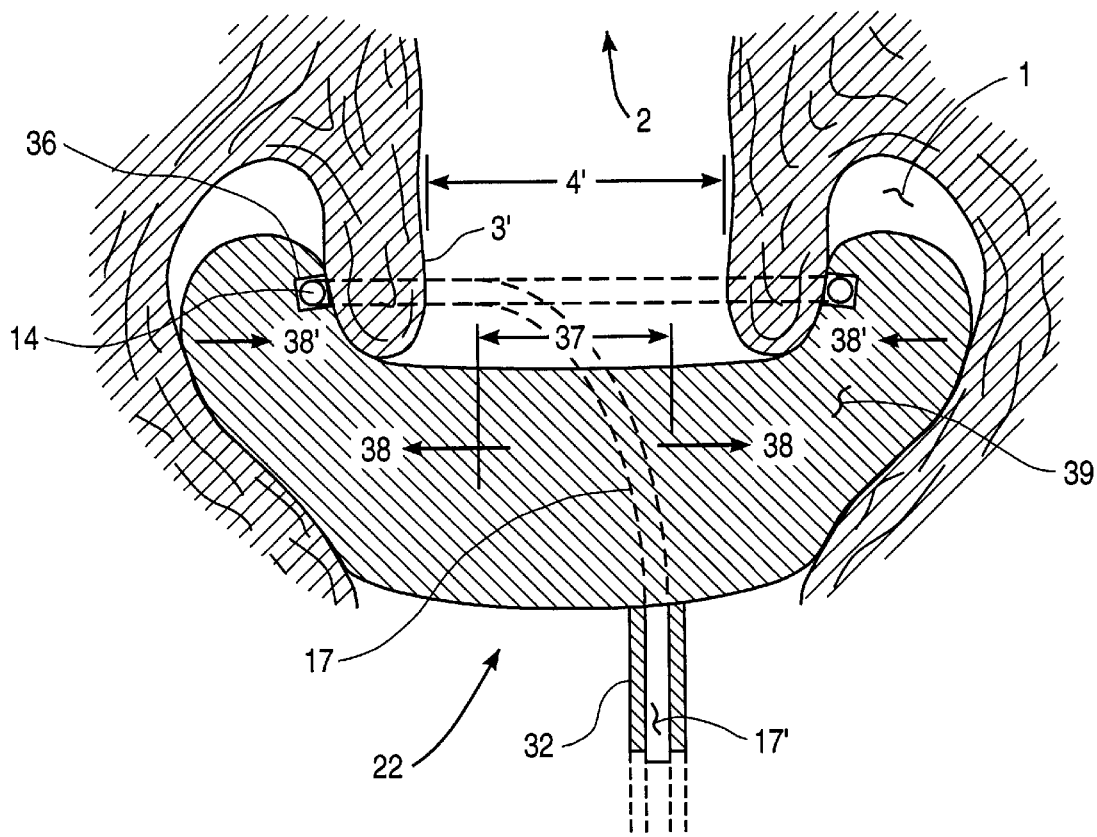
Figure 2E:
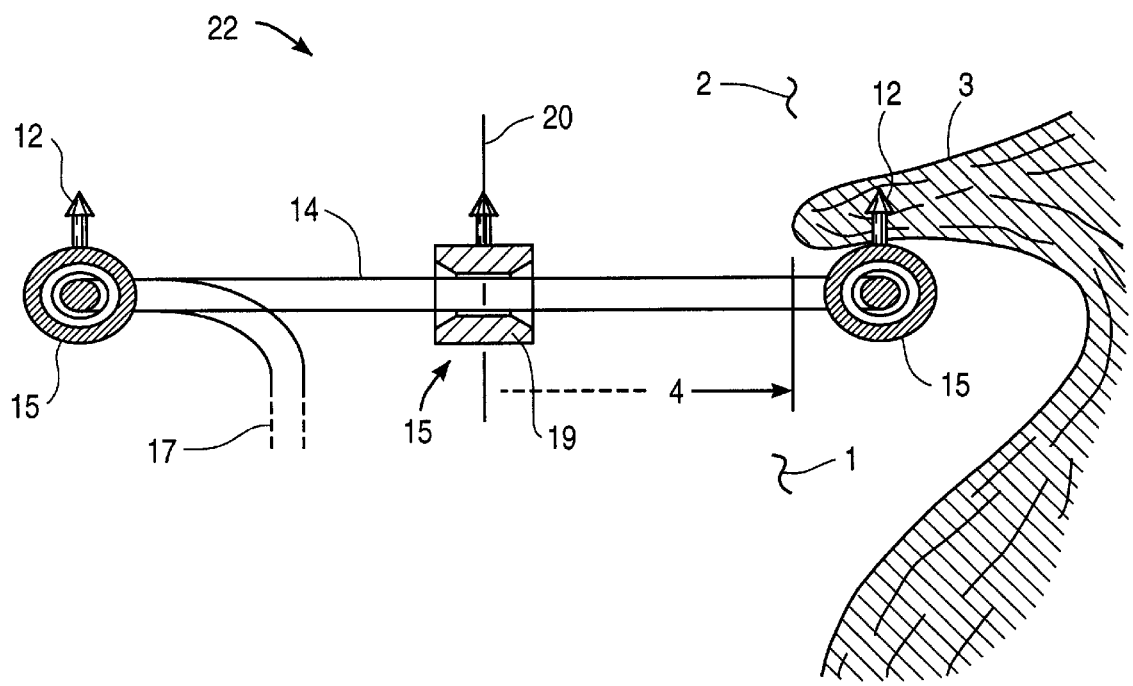

Moving now to FIG. 2A, there is shown a cervimeter system of the circumferential expanding form depicted in FIGS. 2 and 2E which further includes a gauge 23 and other external and likely nondisposable portions of an overall cervimeter system based on wire loop 14 fed-wire. It should explicitly be noted that the state of dilatation in FIG. 2A is substantially less than (earlier in labor than) that of FIGS. 2 and 2E and is indicated by primed cervical tissue 3' and cervical diameter 4'.

Shown are the vaginal cavity 1, uterus 2, interior cervical tissue 3' and cervix dilatation diameter 4'. Given the early state of dilatation in FIG. 2A there is still a tubular shape to the cervical canal as shown (i.e. the cervical canal having dilatation diameter 4' is well defined along its length by a generally tubular interior wall surface 3', as opposed to just a thin lip or membrane 3 as in the earlier figures). It will be noted that the cervimeter device 22 is therein attached to the inner tubular diameter 4' of the cervix and the anchors 15 have their attachment means 12 gripping said internal diameter 4'. It will be appreciated that the anchors 15 may rotate about their local circumferential wire axis and end up in a later stage of labor facing outwards (away from uterus as shown in FIGS. 2 and 2E) if the tissue rotates around with dilatation.

It is noted that additional aspects 1-15 listed above for FIGS. 2 and 2E may also apply to this loop device of FIG. 2A or to any other applicable device herein.

Starting at the top of FIG. 2A, anchor 15' is equipped to accept new wire 17' to be fed into wire loop 14 as dilatation proceeds. Anchor 15' does not necessarily have an attachment means 12. Feedwire 17' is shown surrounded by and slidably contained in a bendable but axially incompressible shell or tube 32. This tube may be fabricated from superelastic nitinol such as Raychem's Tinel™ mentioned earlier. At the bottom of the tube 32 there is a wire-feeding potentiometer 23 attached to, for example, the patients leg 24. Connected to the wire-feeding pot 23 is an electrical cable or related signal and/or power interconnect means 27 running to a wearable reporting module 25. Module 25 is shown mounted on a patients belt 26. The reporting module 25 is shown to incorporate a display 30 and a battery compartment 29. The reporting module 25 is also shown as being capable of transmitting telemetry or telecommunication signals 28 which carry information relating to the patient's or the cervimeter's status. For obvious reliability reasons, the interconnect cable 27 is supported by strain reliefs 31 at their entry points to the components 23 and 25. Signals 28 may obviously be arranged to be incoming as well, which may be used for requesting a data update.

We again stress that for cervimeter device 22 the attachment means 12 (barbs shown) may be any desirable reliable attachment means such as barbs, adhesives or vacuum suction. One may also elect to not use anchors 15 or attachment means 12 at all if the loop can be arranged in the anatomy to maintain its central axis generally parallel with that of the dilating cervical canal as by outwardly (or inwardly) radially biasing the device 22 against an internal (or external) cervical diameter using radial bias applied to wire 14, possibly as by an expanding backer (not shown in this figure) or by the previously shown sleeve 21 of FIGS. 2 and 2E.

The anchor 15' shown serves to guide feedwire 17' into wire loop 14. The tubular catheter shell 32 serves to maintain a known constant spacing (along the flexible wire 17' axis) between the cervimeter device 22 and the wire feedspool/potentiometer 23. It is important to recognize that the use of bendably flexible but axially incompressible catheter shell 32 allows for patient motion and desirable routing of flexible wire 17' to the vagina and accounts for any wire 17' length not either resident in the loop 14 or in the wire spool (or other wire source) 23.

The wire spool/pot 23 may be of any convenient design such as one of the units made for measured wire take-up purposes by SpaceAge Control Inc. of Palmdale, Calif. (see product reference 41). Their 160 series provides more than 40 inches of wire take-up and is only a few cubic inches in size (1.8×1.0×1.6 inches). Their 150 and 173/174 series are even more compact. Model #160-0483-7, with a range of 10 inches, is easily factory modified to a range of 16 plus inches. Since we want to monitor cervical diameter changes from roughly 0–10 centimeters diameter (31.4 cm circumference change or 12 plus inches circumference (length) change) this modification is ideal. One would route their fed metered wire 17' of our design through the sheath 32 of the figure.

It is also important to emphasize that while we show potentiometer 23 serving both the wire 17' metering and wire spool storage functions, one may easily elect to utilize a separate wire feed potentiometer and a separate feedspool. We also emphasize that the pot may take several forms, such as a linear variable differential transformer (LVDT) or a differential variable reluctance transducer (DVRT™- MicroStrain Corp). One might alternatively arrange for laser markings on the wire itself which can be read with an inexpensive optoelectronic component adjacent the wire, the markings indicating location on the wire 17'. In this approach wire 17' itself is a readable scale of a sort.

Reporting module 25 may contain a display 30 as shown for reporting desired parameters such as the present dilatation diameter (shown as 8.7 cm) and a recent dilatation rate (shown as 0.3 cm/hr.). Preset alarm conditions may also be programmed in memory. A compartment for a replaceable or rechargeable battery 29 is also shown as being desirable for portability and ambulatory care. The telemetry or communications 28 shown outgoing from module 25 may, for example, be of any desired digital, analog, microwave, vhf or infrared variety. The outgoing information may also be in audio form as for a synthetic voice annunciation system. A hardwire connection to a separate monitoring system, modem, charging system or other recording/alarming device is also possible (not shown). Module 25 may also record data with time or under preset conditions or may send signals to other devices to administer drugs or therapy.

Reporting module 25 may also be stationed on a bedside shelf or cart, for example, wherein it can afford to be larger, integrate more functions and have alternative use of wall-socket power sources. As an example, the function of module 25 may be integrated into an existing multipurpose patient monitoring device which is connected to a local or wide area computer network (a LAN or WAN) in a hospital. One may also choose to have both the local body-attached monitor 25, as well as a network connection as for an ambulatory hospital patient.

One might arrange for the device 22 and all or part of feedwire 17' and/or catheter shell 32 to be disposable. As an example, consider a potentiometer (or other displacement reading device) 23 which itself does not feed the wire 17' but is capable of reporting wire 17''s passage through it or past it. Using this approach a disposable device 22/wire 17' (and possibly shell 32) may be threaded (fed) into or by such a potentiometer 23 to construct the complete system shown in FIG. 2A.

Moving our attention now to FIG. 2B, we show the same device 22 as shown in FIG. 2A, except that the gauge comprises a visually-read sliding scale. FIG. 2B addresses a very low-cost cervimeter need. Attached, for example, to patient leg 24 (or other body part) is a visual readout scale assembly indicating units of cervical dilatation. The gauge comprises an at least partially transparent outer shell 33 having a scale 34 printed or otherwise marked thereon or therein. Inside of shell 33, which may be made of polycarbonate plastic for example, is sliding wire 17'. As loop 14 changes diameter with dilatation, it causes a change in length of wire 17' resident within scale region 34 of shell 33. Thus, a change in dilatation causes slidable wire 17' and a readout marker 35 fixedly attached to slidable wire 17' to move. The slidable readout marker 35 has an index mark where the reading is taken in reference to scale 34. The use of shell 32 enclosing wire 17' assures that any and all dilatation-induced wire incrementation directly appears on the readable scale. It will be noted that since the scale shown is a linear one, then for 1 cm of diametral dilatation we would have 3.14 cm of circumference or linear length change on scale 34. Obviously, one may mark scale 34 such that one scale unit, corresponding to 1 cm diameter change, is actually 3.14 cm between index marks. This makes the scale easily readable and relieves the reader of the scale of any need to do math. Thus, scale 34 is shown as having marks from 2 to 9 cm of diameter change (shown). One may also utilize a cervimeter 22 to monitor for premature dilatation at home. If this were the case, one may only need a scale indicating a few total cm of dilatation since any significant premature dilatation would call for the patient to go to the hospital and have possible intervention.

The scale 33/34/35 does not necessarily need to be straight or even of a sliding nature. For example a rotating (gauge-like) dial may be utilized wherein the moving wire is arranged to rotate the dial in relation to the dilation. Such a solution would be more compact than the scale shown in FIG. 2B. The point here is that very simple and inexpensive incrementation indicators are useable.

Moving our attention now to FIG. 2C, we again see a loop cervimeter similar to that in FIGS. 2 and 2E; however, there are some major differences. The cervimeter device 22 of FIG. 2C consists of a loop 14 contained (or just constrained) within a channel or groove 36 which runs around the outside diameter of an expandable (e.g. foam) support structure 39. Device 22 is shown mounted in a partially dilated cervix having an interior surface 3' and an interior diameter 4'. The foam support structure 39 is designed to urge the loop 14 into proximity with the cervical wall 3' as arrows 38 indicate. The loop 14 is shown exiting the foam support structure 39 in the previous form of wire 17'. The foam support structure 39 may have an optional uterine access port 37 partially shown in phantom. It will be obvious that if the device 22 of FIG. 2C is utilized one need not utilize anchors 15 (of previous figures) or any other means to separately hold the wire 14 in place.

The expandable support structure 39 may take on any useful shape and expansive tendency (elasticity or inflatability) capable of adapting to different patients cervical or vaginal anatomy or to the changing dynamic anatomy in a given patient. Although structure 39 is depicted as being contained mostly within the cervix diameter 4', designs wherein structure is at least in part resident in vagina 1 (or even in the entrance of the uterus 2 are also anticipated. Multiple initial sizes and/or shapes of backer 39 may be designed, if required, to cover a very wide range of patients as is the practice with diaphragms. Support structure 39 may, for example, consist of an open or closed cell silicone, urethane or polyethylene foam such as the polyethylene foam used in contraceptive sponges for example. Open cell materials tend to allow breathing (gas and vapor exchange) and are generally softer. Foams may be rendered hydrophilic or hydrophobic as the need requires. Foams may be infused with antimicrobial agents if infection is a possibility. Groove 36 may be an open groove or a closed groove and may furthermore be lined with a material different than that of foam 39 which further enhances the sliding action of loop 14 upon the material of backer 39. As an example, groove 36 may be coated or formed of a circumferentially expandable, fluoropolymer material such as teflon. Alternatively, support structure 39 itself may comprise at least in part a slippery fluoropolymer, thus automatically resulting in a slippery groove structure 36. Support structure 39 may also, to a degree, be plastically deformable to custom fit it to the patient. Such a viscoplastic or plastic/elastic device would still be arranged to have expansive elastic properties after installation. Such a plastic form-fitting option combined with the remaining elastic expansive nature after installation may apply to any expansive or pliable backer of this invention.

Expandable support structure 39 may also comprise a composite structure composed of multiple materials. As an example, structure 39 may consist of a foam which primarily offers expansive bias and silicone portions which primarily offer gripping and self-centering features. Structure 39 may alternatively, at least in part, comprise an inflatable balloon, bag or diaphragm whose diametrical inflation provides the desired urging bias forces 38. Foam support structure 39 may contain other perforations or holes (not shown) to further customize the elastic moduli of structure 39 in particular directions. Structure 39 may be arranged to be permeable or impermeable as desired as by the selection of open or closed cell foam materials and the use of impermeable backer coatings such as dipped or cast latex and silicone coatings. It will be evident that, particularly in the case wherein groove 36 encloses wire loop 14 fully, one may easily pull the entire device 22 out of the body without tissue trauma without leaving any parts behind. It is further evident that if labor and delivery proceed to a point where the fetal presenting part is descending and comes in contact with device 22 (it would probably be removed before this) that device 22 will be pushed out of the cervix and/or vagina without any injury to the fetus or the mother.

In the related product area of contraceptive cervical caps and diaphragms utilizing contained spermicide, silicone or natural rubber are used as a structural material and the further use of embedded (sealed) springs to offer resiliency and overall shape control is expected to also be applicable to the construction of expandable support structure 39, thus structure 39 may include elastic spring structures (such as superelastic nitinol) or other plastically deformable members (such as plastically deformable nitinol) to either or both of provide radial bias forces or to allow for a degree of plastic deformation for custom-fitting.

Although device 22 of FIG. 2C is shown to be cylindrical in shape for simplicity, it may be preferred to shape the external surfaces of structure 39 to achieve a desirable degree of self-centering (in the plane of measurement and, optionally, in planes orthogonal to the plane of measurement) as tissues move. Such sculpturing or shaping may be done at the factory or, optionally, may be done by the practitioner after a preinsertion exam. All anatomically desirable shapes of expandable support structure 39 are within the scope of the invention.

Moving our attention now to FIG. 2D, we see a device 22 similar to that in FIG. 2C, except that the device of FIG. 2D is arranged to monitor an outer cervical diameter from the vaginal cavity 1 rather than the cervical diameter 4' from within the cervix. We have previously mentioned that one may choose to monitor a cervical dimension that is correlatable to another dimension of interest. Although cervical diameter 4' is actually the dimension of interest in this example, there may be situations like this in which one would be reluctant to place a device 22 substantially within the cervical canal, (e.g. during ambulatory sensing of preterm labor). Again, a wire loop 14 is shown resident in a channel or groove 36, which in this case runs around an outside diameter of the cervix. We show structure 39 still having an overall outward bias 38, but we also indicate that structure 39 is capable of inwardly urging wire 14 against the cervical outer diameter as indicated by bias forces 38'. It is to be noted again that structure 39 may have any desirable shape and may be composed of multiple materials as described above. It may be resident, at least in part, also in the distal cervical canal (not shown).

As also described for earlier embodiments, wire loop 14, including all needed feedwire to track dilatation diameter over the full desired range (e.g. from 0 or 2 cm to 10+ cm), may be totally self-contained in device 22 itself (not shown) along with the sensing means that reports the amount of fed wire (as fed from an internal spool) or unwound wire (as fed from a multiturn loop 14 which has fewer remaining turns with increasing dilatation diameter. For such a device one would not require wire 17' and sleeve 32 as are shown but would still require an electronic communicating reporting means.

Expandable support structure 39, in a preferred embodiment, would be externally coated, overmolded or otherwise sleeved or wrapped with a rubber film such as silicone or latex rubber to make it leaktight and impermeable yet would consist of an expansive foam or other expansive materials or members in its interior regions. Such a structure 39 may optionally have a uterine access port 37 partially shown in phantom. The expansive mechanism, as mentioned earlier, may optionally be provided for by an inflatable balloon or bag structure utilizing a gas (or a liquid) or by an expansive spring structure.

We will now move to a discussion of radial embodiments of our in-plane cervimeter. Moving now to FIG. 3, an in-plane radial cervimeter 22 is mounted in a partially dilated (early labor) cervix having internal cervical walls 3' and internal cervical diameter 4'. Device 22 is also shown partly resident in vaginal cavity 1. All of the previous comments about expandable support structure 39 preferably being of a more sculptured shape (not shown) apply as usual.

Figure 3:
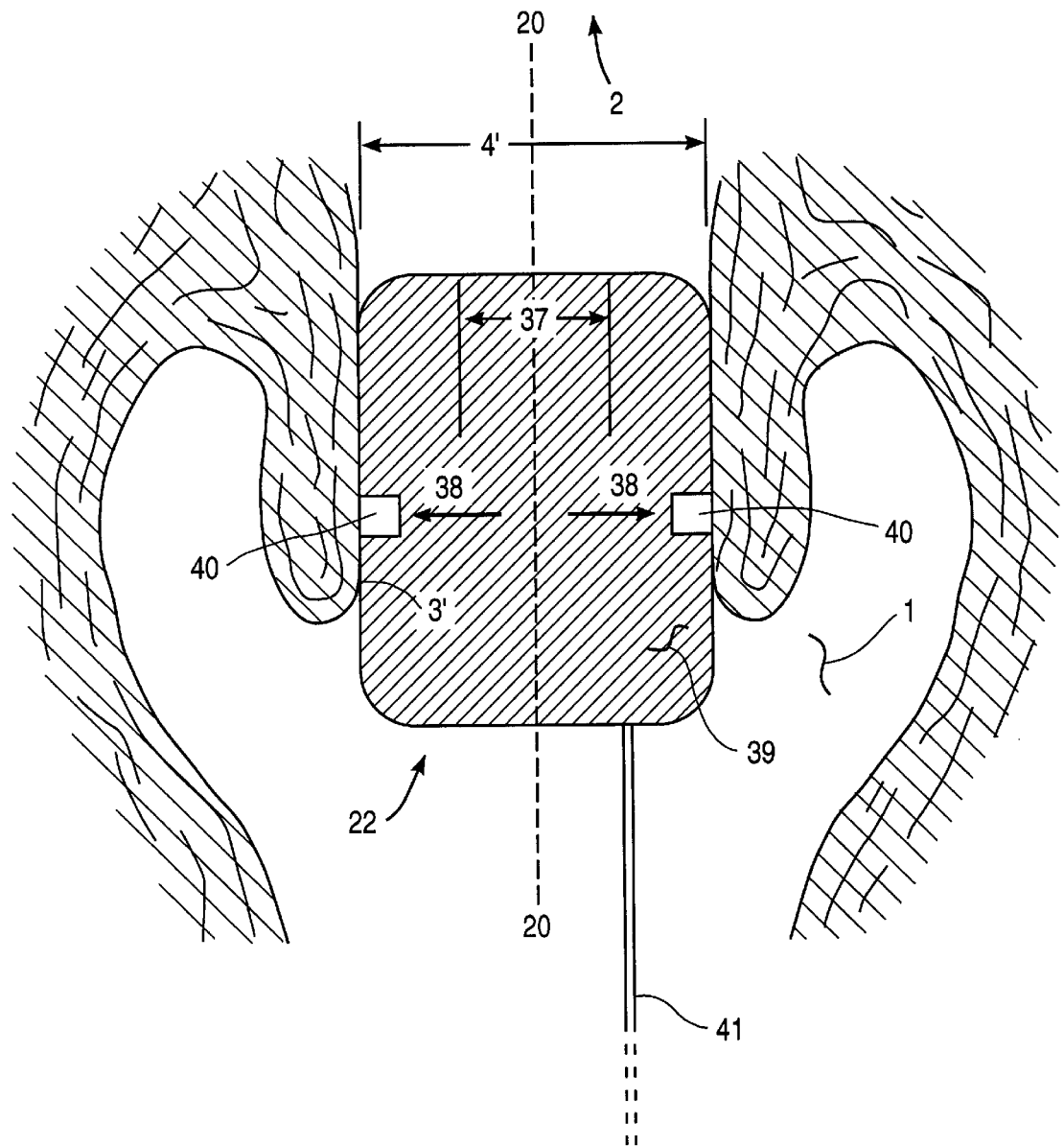
FIG. 3 illustrates yet another cervimeter of the first "in-plane form" utilizing a radially expanding pair (at least two) of location nodes wherein the radial expansion, as urged by an expandable structure, assures that the trackable nodes track a radius, secant or diameter of the dilating os. The nodes may themselves contain resident tracking sensors or, alternatively, the nodes may be trackable using sensors in communication with, or with connection to, the nodes but located away from the nodes.

Cervimeter 22 of FIG. 3 contains two or more measurement nodes 40 urged adjacent to the cervical tissue 3' by the familiar expandable backing structure 39 and expansive bias forces 38. As with the earlier embodiments, the expandable support structure 39 may take on any anatomically advantageous shape and may consist of multiple materials which are elastic, spring loaded and/or inflatable in nature. The structure 39 may be resident in any or all of the cervical diameter, the vagina or partly in the uterus as is desired to achieve the best fit and seating such that nodes 40 will maintain desirable measuring locations.

The measurement node 40 comprises a trackable point, usually near and usually within an outer surface of device 22, which is in mechanical proximity to the tissue surface to be tracked (e.g. near or adjacent 3' and the interior cervical diameter as defined by 4'). By proximity we mean that the node site is mechanically coupled to the adjacent tissue and will move with it and move generally in the same manner such that the node movement can be assumed to generally be the same as that of the tissue movement. The simplest way of achieving this is shown in FIG. 3, namely that the nodes 40 are made resident at the outer surface of structure 39 directly adjacent to the tissue (e.g. 3') to be tracked. The measurement nodes 40 may be locations wherein tracking sensors are located (to be discussed) or, alternatively, may be sites which are trackable using sensors located elsewhere (to be discussed).

An important aspect of the invention is that expandable support structure 39 is arranged so that measurement nodes 40 will track tissue in the desired manner without using barbs or other traumatic attachment means (although these are not precluded). Another important aspect is that elastically adaptive structure 39 may keep the measurement nodes (and incorporated sensor if any) properly oriented despite cervical shape changes and patient motion. Another is that expandable support structure 39 allows one to remove the entire cervimeter 22 as a whole with a simple pulling outwards on the device or its connection means 41 (if any). Another is that unlike prior-art solutions any mechanical loading of tissue is done gently and in a distributed manner such that there is no trauma and such that the cervical diameter 4' is not distorted appreciably by the cervimeter 22. Also structure 39 may be arranged such that retention and loading forces of the type 38 may be applied in other directions (not shown) not perfectly parallel to the plane of the cervical diameter being measured or may be applied such that a tissue squeezing or clamping effect with a component in the direction of axis 20 is achieved (not shown).

Figure 3A:
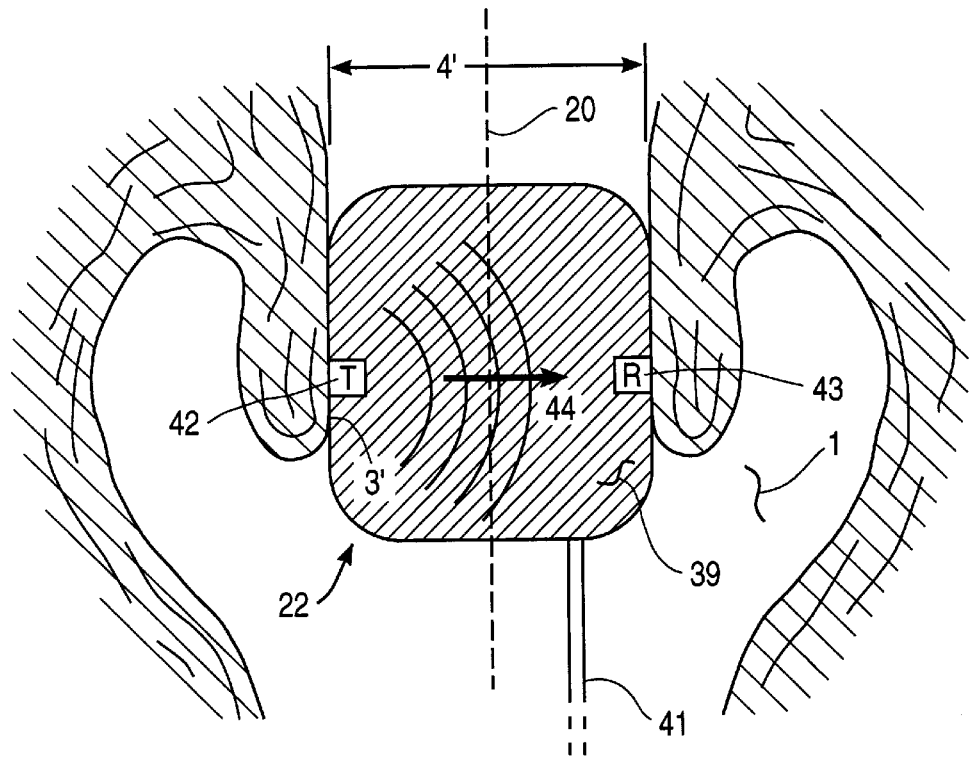
FIGS. 3A and 3B illustrate the in-plane radial cervimeter of FIG. 3 wherein in FIG. 3A one of the sensors transmits a positioning energy field and the remaining sensor receives the field, as modified by distance and position, and deduces the os diameter.
Figure 3B:
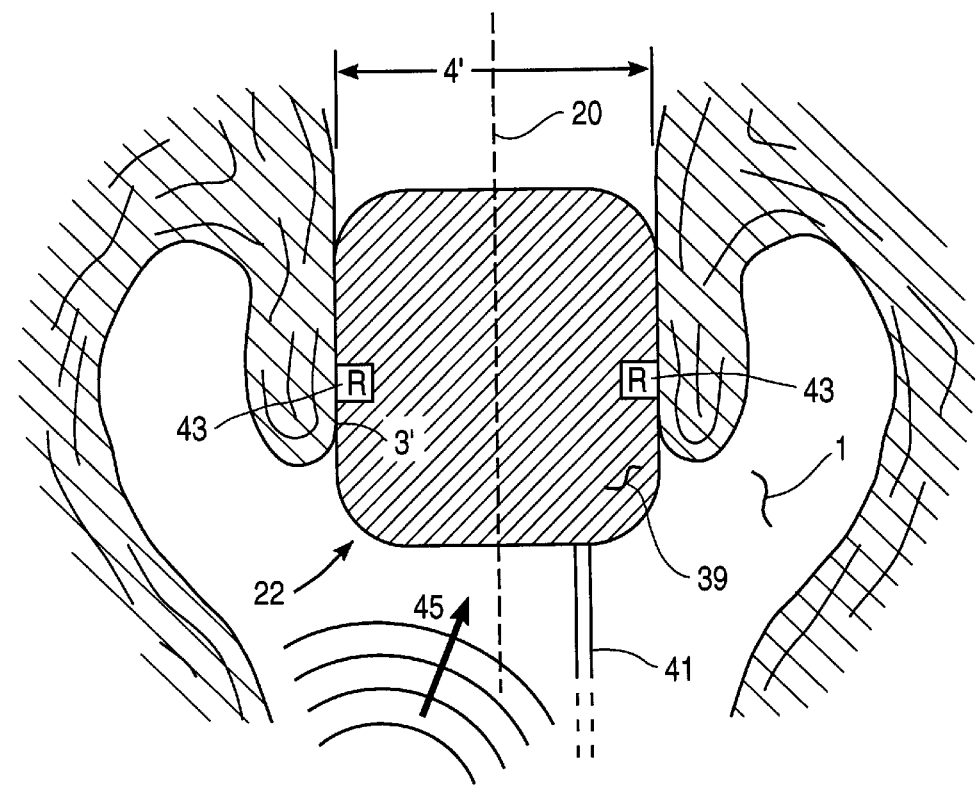

Moving now to FIGS. 3A and 3B, there are shown two specific embodiments of the radial in-plane cervimeter of FIG. 3. In FIG. 3A the left node is occupied by an energy or energy-field emanating or transmitting (indicated by "T") means 42. The right node is occupied by an energy or energy-field receiving (or detecting) means 43 (indicated by "R"). Emanated or transmitted energy 44 from emanating means 42 on the left is arranged to be received or fall upon energy receiving (or detecting) means 43 on the right. The device 22 is shown as having an external interconnect means 41 to provide any externally needed power or signal connections. The transmitting and receiving (or detecting) means are arranged such that the distance between them modifies a characteristic of the propagating energy or energy field 44. As an example, if transmitting or emanating means 42 were a permanent magnet or electromagnet its magnetic field would fall off as a known function of distance thus giving an indication as to the distance to receiving means 43. In this case, the receiving means 43 might consist of a Hall effect, magnetoresistive, flux-gate or magnetoinductive sensor capable of measuring static (or dynamic) magnetic field strength imposed from transmitting means 42. A nonmagnetic example would be the case wherein transmitting means 42 is an optical source and the light intensity is modified as by attenuation or simply distance and receiving means 43 detects the reduced intensity as with a photodiode. If one wanted to have an access hole through device 22 for access to the uterus (hole 37 of prior figures), then a form of energy or energy-field, such as an electromagnetic field, should ideally be chosen which will not be disturbed by such a hole. It is important to note that structure 39 assures proper orientation and placement of both the transmitting means 42 and the receiving means 43 without trauma. A significant failure of the prior art was that such sensors and transmitters were allowed to flop around even though they are not omnidirectional. It will also be obvious to one skilled in the art that any number of transmitting and receiving sensors may be used and that the locations do not necessarily have to represent diameters of the cervix. For example, two nodes could measure a chord of the circumference and the diameter could be computed using trigonometry, knowing their angular location on structure 39.

Moving now to FIG. 3B, we have a very similar in-plane radial cervimeter 22 as in FIG. 3A; however, in FIG. 3B the two shown nodes 43 are each occupied respectively by a receiver. Receiver means 43 is shown on the left node and another receiving means 43 is shown on the right node. It will be noted that transmitted or emanated energy 45 impinges on both receivers of the type 43 in the figure and that the energy (or field) 45 is received or sensed emanating from a location other than either of the shown nodes. In fact, emanated energy 45 is shown coming from below (in the figure) cervimeter 22 of FIG. 3B. An intrinsic advantage of the arrangement of FIG. 3B is that one might arrange for receivers 43 to be passive in nature such that they require little or no external powering and present little or no concerns regarding shock hazards. Another intrinsic advantage is that the required transmitting or emanating means (not shown) emanating energy or field 45 may be resident outside of the body. Thus, it may be more complex, more bulky, nonbiocompatable and nondisposable and may be capable of far higher power or field emanation and could even serve more than one patient.

A preferred embodiment of the radial in-plane cervimeter is that of FIG. 3B wherein the spatial tracking system consists of a magnetic spatial tracking system as are widely used in virtual reality games, cartoon animation and military head-tracking gunsights. Such systems are made by companies such as Polhemus (Polhemus Inc., Burlington, Vt. 802-655-3139) and Ascension (Ascension Technology Corporation, PO Box 527, Burlington, Vt., 802-860-6439).

Specific models which are useable herein include but are not limited to: Flock of Birds™ (Ascension) and IsoTrak2™ and Fastrak™ (Polhemus). These sensors can detect and report six degrees of freedom (x, Y, Z, $0_1$, $0_2$, $0_3$).

In essence, such a tracking system consists of an electromagnetic transmitter capable of emanating DC or, alternatively, AC magnetic fields 45 of FIG. 3B. The transmitter (not shown) consists of a cube about 2 inches on a side and contains three orthogonal coils used for transmitting three orthogonal, probing fields. The receiver(s) 43 may be singular or may be many (up to 20 or 30 for example) and each receiver internally consists of three orthogonal small sensing coils. Two such receivers (each containing three orthogonal receiving sensing coils) are represented by the two items 43 in FIG. 3B. The transmitter emanating field 45 causes very small but detectable electrical response (a sensed voltage and/or current) in each sensing coil of each receiver 43. Given that one may transmit fields in three orthogonal orientations (as by switching between transmitter coils) and may sense or receive the components of each of the three transmitted fields sequentially using each of the three orthogonal sensing coils in receiver (s) 43, one may determine the strength and orientation of the three emitted magnetic fields at the location of each receiver 43. The strength and orientation of each transmitted field is a known function of receiver 43 distance and orientation with respect to the transmitter. Thus, receiver 43 distance and orientation with respect to the transmitter may be routinely computed using matrix mathematics as implemented in software, firmware or hardware.

In the cervical diameter 4' measurement application of FIG. 3B we utilize such a magnetic spatial position tracking system to locate the two (or more) receivers 43. It will immediately be obvious that one may then easily determine the distance between sensors or receivers 43 using trigonometry knowing each of the two receivers 43 locations and orientations. The computed distance is equal to the dilatation diameter (for FIG. 3B) which is the desired parameter.

The magnetic spatial locating systems from Ascension or Polhemus described above can be arranged, ideally in combination with a computation device such as a personal computer, to compute, record and graph the true distance between the receivers while accounting for any unpredictable angular orientation changes of the receivers in a transparent manner. The PC is used to compute the separation distance of the receivers 43 via a simple trigonometric software algorithm (square of distance equals the sum of the squares of delta x, delta y and delta z respectively) for computing the distance between a point x1,y1,z1 and a second point x2,y2,z2. Thus, prior-art errors due to sensor angulation, are both minimized (by the beneficial orienting and stabilizing effects of structure 39) and accounted for (by the spatial magnetic tracker system). Since these unique receivers are not negatively affected by angulation (with respect to delivering reliable X, Y, Z positions) we also specifically include herein an embodiment wherein such receivers are attached to the tissue structures without the aid of structure 39, as for example with conventional barbs or clips or a spring-loaded clamping device.

Since in our example of FIG. 3B using the magnetic spatial positioners we need only measure the distance between the receivers 43, we do not have to necessarily keep the transmitter (not shown) stationary nor keep the patient stationary between measurements each of which takes a very short time on the order of milliseconds. Thus, one may arrange for the transmitter to be carried in a belt or other ambulatory carrier system as shown in earlier FIG. 2A. The transmitter may also be placed by the bedside. In either case the patient may move her body without disrupting the measurement capability. We also mention that because we are using an external transmitter in this embodiment, we are capable of overpowering any ambient electronic or electromagnetic noise as is frequently found in hospitals. The duty cycle of measurement (readings per unit time) may be kept small as cervical dimensions change slowly.

It will also be obvious to one skilled in the art of spatial position sensing that numerous modifications may be made to the above Ascension/Polhemus examples. For example, one may utilize receivers 43 which, instead of utilizing wire-wound coils, utilize thin-film, chip-mounted, planar coils. Such chip-based magnetoresistive sensors and their supporting systems are available, for example, from Honeywell Inc. Useful devices include but are not limited to: Honeywell Inc, Solid State Electronics Center, Plymouth, Minn: Models #HMC1001, HMC2003 and HMR2300.

Since the described commercially available magnetic spatial positioning systems may handle numerous receivers 43, we specifically include an embodiment wherein in addition to (or in place of) cervical measurements one mounts receivers 43 at other sites of interest. As an example, one could mount a receiver on the fetal presenting part, usually the skull, and report the station of the descending fetus relative to any other body-attached receiver 43 or relative to the transmitter.

FIGS. 3A and 3B also incorporate the expandable support structure 39 discussed previously. Biasing forces are not shown for simplicity. We again stress that the shape and material composition of structure 39 may vary depending on the anatomy and dynamic anatomy-adaptation needs.

Figure 3C:
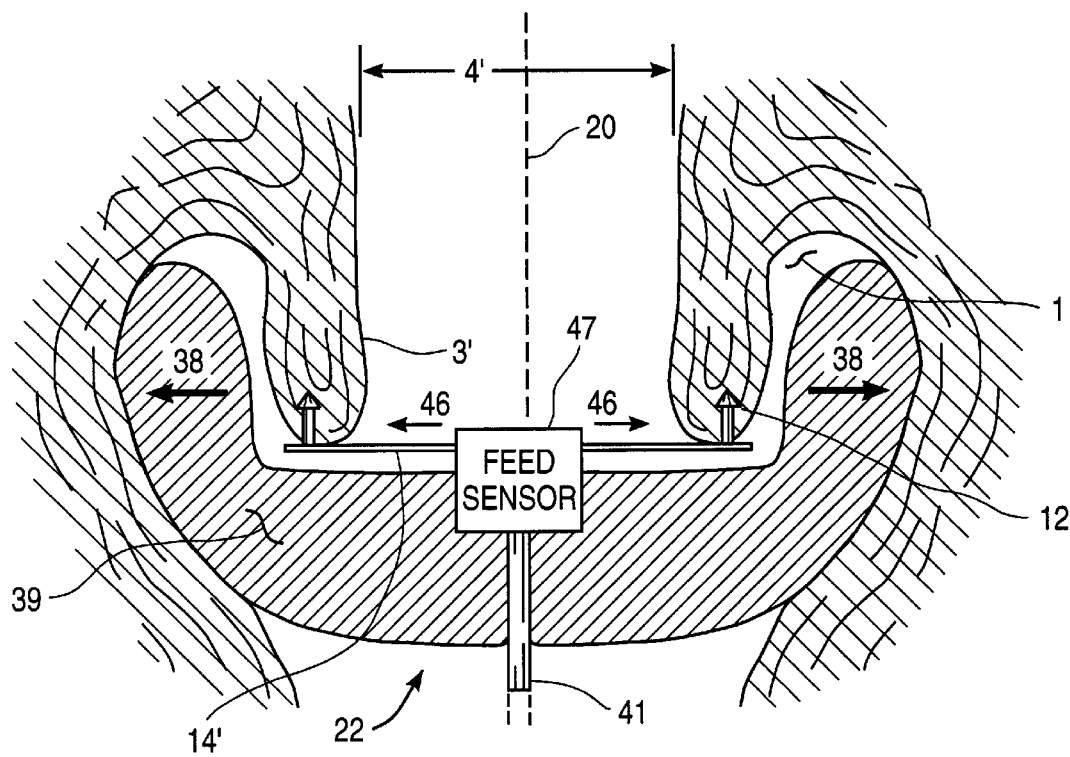
Figure 3D:
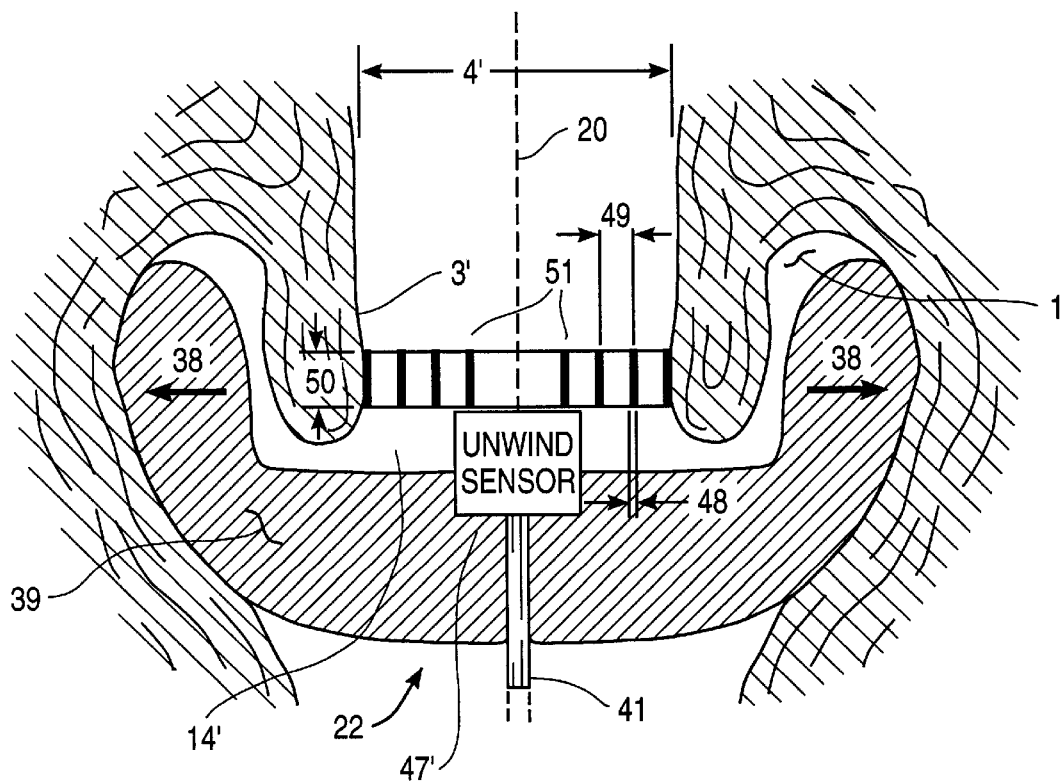

Moving now to FIGS. 3C and 3D, there are shown two additional embodiments of a radial cervimeter of this invention. Beginning with FIG. 3C, a cervimeter 22 comprises expandable support structure 39 to grip the vaginal (shown) and/or cervical (not shown) tissue surfaces. Shown are radial wires 14' each attached to the dilating cervical tissue 3' using a barb 12 or any other convenient fixation means. As dilatation proceeds and cervical diameter 4' increases in directions 46, wires 14' are withdrawn in the radial directions 46 from the central axis region 20. A sensing means 47 is provided capable of measuring the increments of wire 14' moved in directions 46 and reporting the increments. Feedwire storage (not shown) may, for example, be in the region of sensor 47 or may be outside of (below in the figure) cervimeter 22 in the outer vagina or outside the body as for the device depicted in earlier FIG. 2A. It will be obvious that barbs 12 or their equivalent attachment means may be attached anywhere around the cervical lip region as long as the amount of initial wire at time zero can either be accounted for or zeroed out. Wires 14' may be presented to the cervical tissues 3' while temporarily attached to a membrane carrier (not shown) in order to preserve their proper spacing until such attachment has been achieved. An interconnection means 41 provides any power or signal (or possibly wirefeed 14') needs. Radially expansive bias forces are indicated by arrows 38 indicating that the device will continue to seat itself properly even if the vaginal walls expand. The "wire" 14' of FIG. 3C may take on any form such as monofilament, multifilament, stranded, nonstranded, wound, unwound, round section, rectangular section, solid, hollow etc. Wire 14' may also be made of any one or more useful materials such as stainless steel, nitinol shape-memory alloy, beryllium copper, polyimide or metallic foil. A preferred embodiment for the "wire" 14' utilizes superelastic nitinol wire of round cross-section with a diameter between 0.003 inches and 0.010 inches.

Moving now to FIG. 3D, there is shown yet another radial cervimeter 22 also using an expanding support structure 39 to grip the tissues. In this cervimeter, rather than having unreeling or fed wires 14 or 14' we have a coiled spring which uncoils against the cervical inner diameter 4'. The coiled spring material is rectangular in cross-section with a cross-sectional thickness indicated by 48, a cross-sectional width indicated by 50 and a coil spacing 49. For the sake of pictorial simplicity, the coiled spring is shown with a constant sectional width 50, thickness 48 and spacing or pitch 49. In fact, the coil may have a variable thickness and/or width and/or pitch. It will be noted that the coiled spring has several windings where the cross-section is observable such as at locations 51. In the figure, approximately four wrappings or turns of the coiled spring are depicted. The coil may be mechanically radially restrained until it is inserted in the cervix, then allowed to unwrap (uncoil) against the cervical wall 3'. Alternatively, if nitinol is employed, the heat of the patients body may be allowed to unwrap the coil and place it against the cervical inner diameter 4'.

Various gauges may be employed to detect the degree of coil unwinding and, therefore, the cervical diameter 4'. Those familiar with coil springs know that for a given amount of wrapping tension imposed by a diameter 4', the individual wraps assume predictable equilibrium relative positions and curvatures. Thus, for example, if the coil spring had strain gauges mounted on certain of its bendable (e.g. width 50) surfaces, those curvature(s) could be monitored and the coil diameter (4') could be computed from the known stress vs shape behavior as determined experimentally during device design.

It will also be apparent that device 22 of FIG. 3D may employ one or more unwinding or unbending springs of alternative radial design to that shown in FIG. 3D. For example, one could curl several spoke-like radial springs around axis 20 or otherwise radially compress or bend one or more such springs. As the diameter 4' increases, the degree of wrapping, curling, bending or compression of the springs decreases. One could likewise instrument one or several of such springs to deduce and compute the average spring curvature and, therefore, the average cervical diameter 4'. An "unwind" sensor 47' is shown in FIG. 3D which may, for example, route the strain gauge voltages to the outside world or convert said voltages to diameter 4' locally.

We specifically include embodiments wherein the spring material itself offers an indication of its degree of curvature for a known geometry and bending mode. As an example, the electrical resistivity of certain materials is a function of the elastic stress and so the curvature may be deduced from the electrical resistance measured along the length. The optical losses and mode modifications of many optical fibers are a function of bending of the fiber and likewise an optical fiber spring's curvature could be optically deduced from the losses or optical mode changes along the bent fiber. More specifically, as reported in Brudin, Photonics Spectra (January 1996), page 106, one may utilize fiber-bragg gratings. These fiber devices alter an ingoing wavelength in a predictable manner in response to stresses on the fiber.

Finally, with respect to FIG. 3D, the spring(s) structures may consist of bimetallic springs or piezo bimorphs. In the case of a bimetallic spring, such as a beryllium copper/stainless steel laminate spring, the human body could provide the heat which causes the spring(s) to uncurl and touch the tissue. One could then still, for example, utilize strain sensors to deduce the degree of bending and therefore the cervical diameter 4'. In the case of a piezo bimorph one utilizes a piezomaterial laminate which bends in response to a voltage. In this manner the bimorph springs could be uncurled using a voltage bias (or curled) to bring them in contact with the tissues. Then either a strain sensor or the bimorph itself (via a bending induced voltage for example) could be used to sense bending and therefore diameter 4'.

Figure 4:
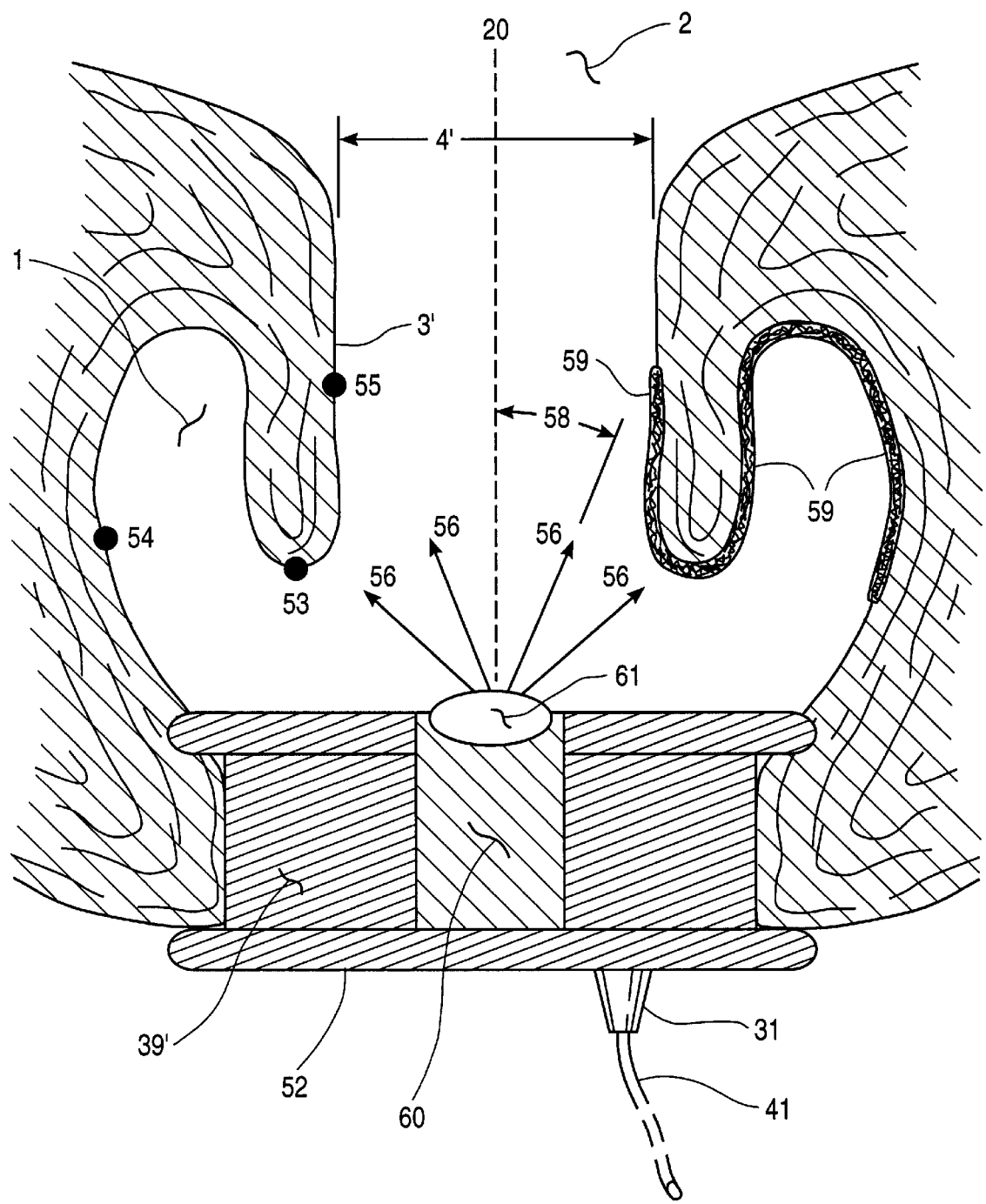
FIG. 4 illustrates a second form of the cervimeter invention, referred to as the orthogonal form, wherein an energy or field emission and reception means is arranged to generally orthogonally measure the cervical diameter. The cervical structures may optionally be marked with markers or sensors to benefit the ease of the measurement.

We now move to a discussion of the second major form of the invention, the orthogonal form, wherein the cervical structures are measured from one or more orthogonal planes oriented generally perpendicular to the cervical diameter(s) or dimensions of interest. A first generic form of the orthogonal device is shown in FIG. 4. In the figure the familiar vaginal cavity 1 and cervical canal with diameter 4' and inner wall 3' can be seen again. Shown again is an early stage of dilatation wherein the cervix is still of a tubular shape near the vagina. Mounted in the entry of the vagina is an orthogonal cervimeter 52 having an interconnection cable 41 and strain relief 31 as seen earlier. Cervimeter 52 has a body 39' which may be, at least in part, elastic and conforming to the body to ensure patient comfort and a good grip. Cervimeter 52 may have one or more access ports of the earlier type 37 if desired (none shown). Integrated within the cervimeter 52 body 39' is at least one module 60 containing energy or field- emanating or transmitting means and/or corresponding reception means. Such emanated energy is shown as emitted energy 56. In the case of energy 56 consisting of directable energy, an emission angle 58 for a particular directable energy ray may be defined. Also shown is a lens or window component 61 which may serve to focus the energy in a particular selectable direction(s) such as at angle 58. Additional beam steering means (to steer in at least one such orthogonal plane) may be included in or together with module 60 such that the combination of steering means and lens 61 allows for steering focused energy. Multiple energy rays are shown generically to indicate that the device 52 may selectively steer its probing energy to tissue points such as 53, 54 or 55 or, alternatively, may emit the energy over a wide angle in a nonselective unsteered manner. Generically, the same applies to reception of energy; the device may receive from selected angles 58 or from all angles simultaneously.

Also shown on a portion of the interior tissue walls of the vagina 1 and cervix tissue 3' is a tissue surface modification 59. As will be discussed the modification 59 may optionally serve to aid the cervimeter 52 in making its measurements as by controlling reflectivity of the tissue or offering a surface with images projected thereon (such as graticules) whose distance can be deduced from their apparent projected size and/or distortion. Energy rays may simultaneously be emitted and received as in an example wherein a laser beam is both transmitted and then received after reflection. The lens (or window) 61 may be heated to reduce fogging, if any. A disposable sheath having a suitable window for energy passage could also be used (not shown).

Moving now to FIG. 4A, we will discuss specific embodiments of the orthogonal cervimeter 52 of FIG. 4. In FIG. 4A we have an optical transmitting source 62 labeled as "T" and an optical receiving source 63 labeled as "R". Also shown are two reflectors 64 mounted to the cervical tissues at opposite points such that the imaginary line connecting them represents a cervical diameter to be measured. It will be noted that the reflectors 64, spherical ball reflectors in this case, will always reflect back to the receiver 63 regardless of its position. Miniature corner-cube retroreflectors 64 could also be used. The mode of operation is as follows. A transmitter 62 in a first position illuminates the reflectors 64 and the light reflected from the reflectors 64 is detected by a receiver 63. Then the operation is repeated by having transmitter and receiver switch positions as by electrical switching (in other words each of items 62 and 63 are capable of both transmission and reception). Given the known distance between 62 and 63 and detection of the angles at which each of the reflectors 64 is viewed from each of the two positions, one has enough to trigonometrically compute the distance between the reflectors 64. Alternatively, one could have an independent illumination source 62 and dual receivers 63 allowing for simultaneous stereo imaging and cervical dimension computation. It will be noted in FIG. 4A that the reflectors may be attached to monitor the motion of any two (or more) tissue points, and in the case shown the points are somewhat outside of the indicated cervical diameter 4'. It will be recognized that the receiver 63 need only detect the angle at which reflections appear. Although this could be done by an area-wise imaging (television) chip, it could also be done, at least in one plane, using a simpler CCD chip with a single row of detectors and a lens as available from Reticon Inc. (EG&G Reticon Inc., Sunnyvale, Calif. 408-738-4266) or Hammamatsu (Hammamatsu Corp., N.J., 908-231-0960). It will be obvious that one might also attach such a reflector 64 to the presenting part of the descending fetus to determine fetal position or station. The illumination may be selected so as to maximize reflection selectively from the reflectors and to minimize it from other tissues. One might also coat the reflectors with a fluorescent material so that a short illumination causes them to be fluorescent after the illumination is turned off. In this manner, the fluorescent illumination is detected selectively totally independent of the tissue. Other permutations of reflectors 64 may, for example, utilize reflectors which are in strip form and are attached along a length of tissue or an array of reflectors mounted to the tissue on a temporary carrier.

Moving now to FIG. 4B, we again have one or more receiving imaging devices this time labeled as 63. The transmitting device 62 consists of an optical fiber which is routed into the cervix. (At least the light, if not the fiber itself, is directed into the cervix). The mode of operation is as follows. Since the optical fiber light is selectively directed into the cervix, then from the viewing position of the receiver 63 only the cervix is lighted significantly. The receiver device(s) 63 again may consist of an imaging chip. By using dual separated receivers 63 as shown one may again use triangulation or stereo imaging to determine the cervical diameter 4'.

Moving now to FIG. 4C, we have a transmitting device 62 which, in this device 52, is projecting an image of a graticule such as a grid array on the interior tissue walls. A portion of such a projected grid pattern is indicated as item 65. Again we also have a receiver device 63 capable of imaging the projected graticule 65. Such a receiving device may be an areal CCD imaging chip giving a video or TV image as mentioned earlier. It will be apparent to one familiar with image projections that structured light topography measurements of the tissue topography will distort the image of the graticule or mesh pattern (shown) in a way which is directly dependent on the distance and angle of the tissue to the projector. Thus, a computer means may quickly map the tissue surfaces and dimensions by examining the apparent projected distortions and size of the graticule patterns. Optionally, one may choose to alternate positions of 62 and 63 or may choose to have multiple items 62 and/or 63. It will also be obvious that the graticule pattern need not be regular, may be spatially encoded, and may be changed depending on the need.

Moving now to FIG. 4D, we have another orthogonal device 52, this time utilizing optical triangulation principles. Specifically shown is a transmitting device 62 emitting a laser beam 66A which is reflected as beam 66B back to a receiver device 63. If the transmitter and receiver are each arranged so as to record the angle at which the laser beam is emitted or received it will be obvious that the tissue point where the light was reflected is spatially known with respect to device 52 through trigonometry. Again one may switch positions of the transmitter and receiver during measurement and may use a receiver chip which is a full areal TV or video imaging chip. In the case of an areal TV or video imaging chip receiver 63, the transmitter 62 may be arranged to be capable of scanning the laser in multiple orthogonal planes or in volumetric space. Laser triangulation metrology devices are becoming widely available from companies such as Anritsu America of Rochelle Park, N.J. and MTI Instruments of Latham, N.Y. In order to facilitate the invention, one would arrange for a device such as these to be further miniaturized and selectively angulated.

Moving finally to FIG. 4E, we have an orthogonal cervimeter somewhat similar to that in FIG. 4B. However, in FIG. 4E a length (or loop) of illuminated optical fiber is imaged. Specifically shown are a transmitting optical fiber 62 whose outer surface is illuminated (optically leaky) such that at least its loop 62A is clearly optically delineated. The loop portion 62A is shown unwinding within the cervical diameter 4'. Receivers 63, which again may be imaging CCD chip, image at least the illuminated loop 62A. It will be obvious that if the optical fiber can be imaged by two such receiver imaging chips 63 then the size and location of the optical loop may be computed. The optical loop may be arranged in any useful form such that it touches the tissue of interest or expands along with a diameter 4' of interest. The optical fiber may have localized spots of light emission at fixed distances to each other (like a scale) as opposed to having its entire length illuminated. The loop may alternatively consist of one or more unbending illuminated radial spokes as well.

For all of the embodiments 4A-E of this first generic form of our orthogonal cervimeter we emphasize that variations do not depart from the nature of the particular solutions. For example, for the purposes of any imaging or receiving means 63, one may choose to utilize an external camera chip and route its fiber optic imaging bundle to the indicated receiver 63 location. Such an imaging chip might be a CCD chip or might be a newer CMOS imaging chip. The same may be said of a beam or image transmission device 62. One may utilize a fiber bundle and lenses such that one or more stationary or moving beams or images may be delivered via location(s) 62 and into the cervical structure but be created outside of the body. Although we have referred to imaging chips as "CCD, CMOS, video or TV imaging chips" one skilled in the art will know that we need only frame-grab selected occasional images with such imaging chips (2D imagers or 1D linear imagers) and not necessarily create a streaming continuous duty-cycle viewable video image. It should also be obvious that for several of the devices discussed here, for example those of FIGS. 4A, 4C and 4D in particular, that device 52 may be removed from the body if necessary and later replaced without concern as to perfectly relocating the device. This might be needed, for example, if the fetus is to be worked with or if the patient needs to conduct personal hygiene care. By the same token these devices are insensitive to patient motion.

One may also utilize any convenient optical wavelengths of illumination for the cervimeters of FIGS. 4A–E. Multiple separate spectrums may be delivered to enhance particular features. Particular wavelengths may also be delivered which additionally offer a diagnostic optical imaging purpose in addition to the dimensional measurement purpose. Optical energy need not necessarily be in the visible spectrum, as for infrared illumination whose reflection gives substantial information regarding blood presence and oxygenation.

Several of the devices, such as those of FIGS. 4C and 4D, will do an excellent job of imaging the topography of the descending fetus (and its station) in addition to determining cervical dimensions and tissue surface topography.

The orthogonal cervimeters may also employ stereo imaging, optionally utilizing projected structured light. Such technology is described generally in references, such as Blatt et al. (1992) SPIE 1821:304–311. Guisser et al. (1992) SPIE 1821:394–404, and Starks, manuscript entitled STEREOSCOPIC IMAGING TECHNOLOGY, which has been made of record in this application. Such stereo imaging techniques may be used to obtain information on both size and shape of the cervix.

Figure 5A:
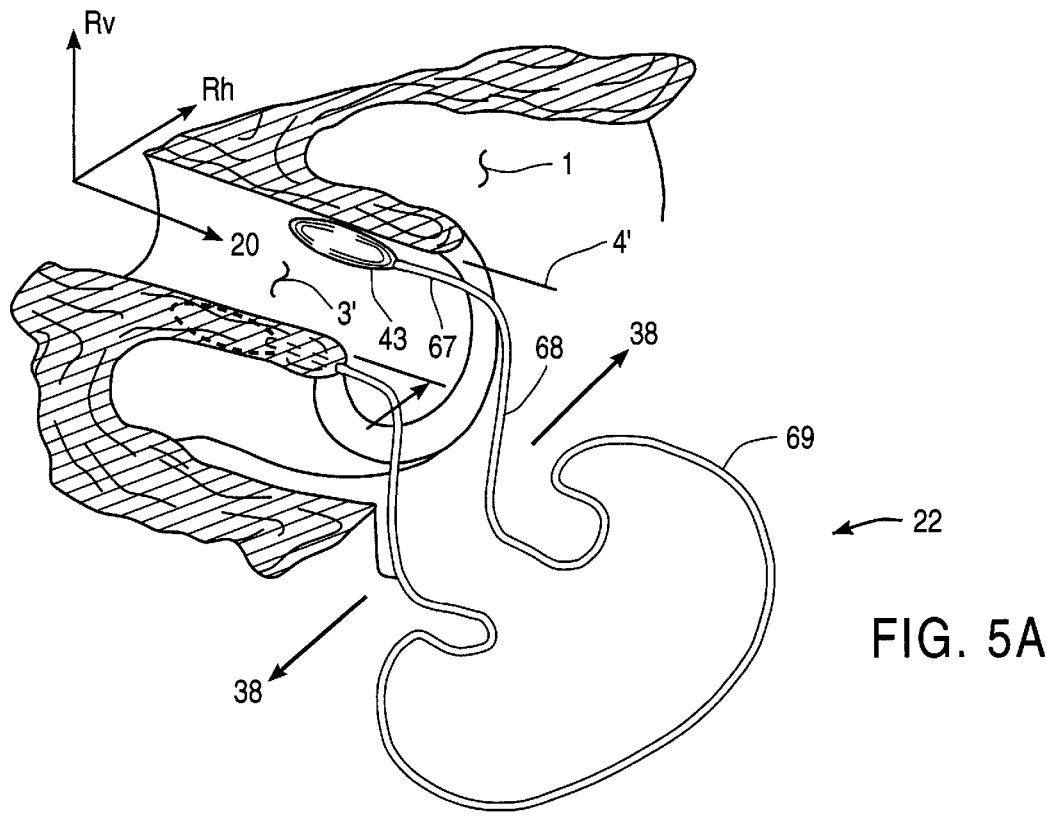
FIGS. 5A and 5B illustrate two variations of a second arrangement of the second (orthogonal) form of the cervimeter invention, wherein an orthogonal mechanically expandable spring structure urges tracking sensors to contact and follow the dilating cervical tissue.
Figure 5B:
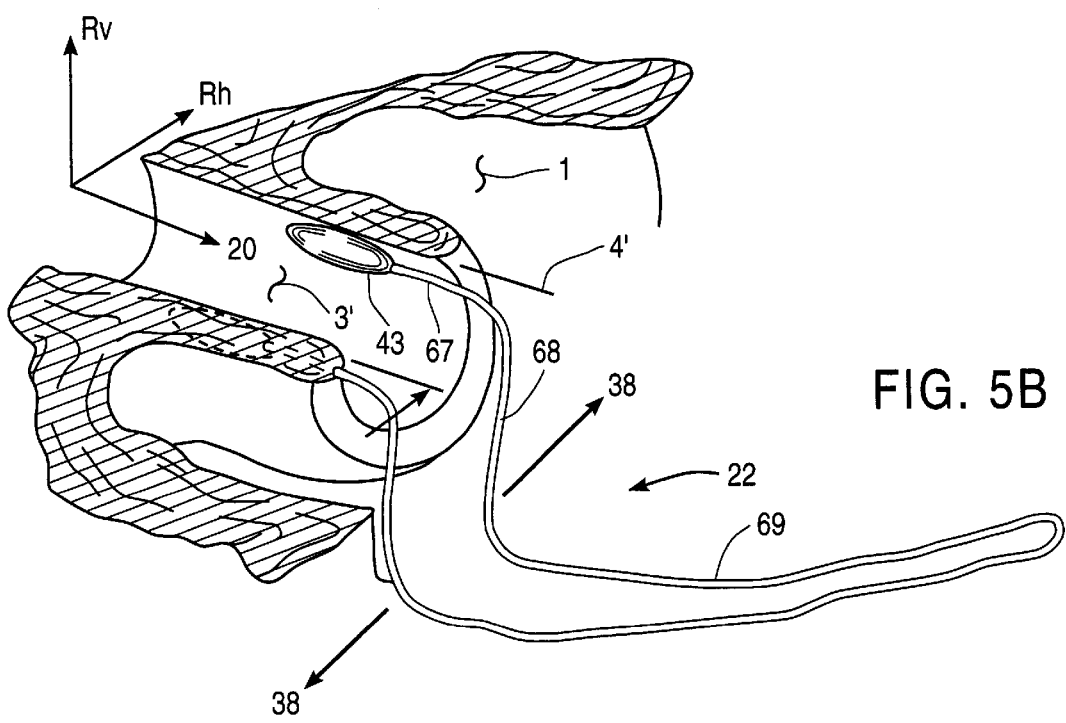

We now move to FIGS. 5A and 5B which depict two variations of another form of the orthogonal cervimeter 22. In this form the orthogonal expansive means urging the tracking sensors 43 against the cervical tissue surface 3' consists of an orthogonal spring structure. Both FIGS. 5A and 5B are shown in isometric view, unlike previous figures, in order to best show the three-dimensional nature of the expansive spring 67/68/69. A spatial coordinate system is also shown wherein the familiar cervix axis 20 is seen as well as two radially oriented additional axes Rh (horizontal) and Rv (vertical). Electrical interconnections to the sensors 43 are not shown for simplicity.

In FIG. 5A one sees the familiar cervical diameter 4' and cervical tissue 3' of a partially dilated cervix. A spring structure 67/68/69 is shown resident in the body. The depicted spring consists of three primary parts. The first parts 67 are the portions actually reaching into or onto the trackable surfaces 3' and supporting the tracking sensors 43. These are generally parallel to axis 20 as shown. The second parts connected to parts 67 are vertical riser portions 68 generally parallel to axis Rv as shown. These serve, in part, to keep the cervical entry clear for other access. The third portion 69 shown situated on or in contact with the floor of the vaginal cavity and very roughly in the Rh/20 plane is the primary expansive portion of the spring in this example. Outward and generally radial bias forces of the familiar type 38 are shown keeping the shown magnetic receiving sensors 43 adjacent the trackable tissue during cervical dilatation. The spring structure 67/68/69 may take on numerous forms and be fabricated of numerous materials. A preferable material is superelastic nitinol as is widely used in medical catheter and guidewire construction. The advantage of superelastic nitinol is that very large strains or bending curvatures may be imposed on such a spring structure without causing plastic yielding or kinking. Alternatively the plastic form of nitinol could be used wherein the heat from the human body drives the spring structure to track the growing cervical dimension via its tendency to return to a more open "programmed" state. Such heat-treatment "programming" of nitinol using mandrels to "program" the memorized shape are widely known and utilized. In a similar vein one might utilize a bimetallic laminate at least for spring portion 69 which naturally desires to bend open due to the differential expansion bending caused by body heat.

It will immediately be obvious to those skilled in the art that other springy materials such as stainless steel, plastics and even some bendable rubbers and foams may alternatively be utilized and that spring portions 67/68/69 may be joined segments of different materials each possibly having different cross-sectional shapes. Portions of the spring may be coated as with silicone or latex. It will also be obvious that spring portion 69 (and possibly 68) may be arranged or routed such that they bear on vaginal or cervical surfaces in a manner offering retention of the device 22 portion 67 adjacent the cervical inner diameter 4'. Indeed device 22 spring portion 69, as shown, will tend to be pushed toward the back of the vagina (toward the cervix) by the contacted front surfaces of the vaginal cavity (not shown). Although spring 67/68/69 of FIG. 5A is depicted deforming primarily in bending roughly in and parallel to the Rh/20 plane, it is expected that other forms of bending such as torsion may be utilized. Thus by spring we mean any entity which demonstrates the desire to deform in a manner allowing for cervical diameter 4' tracking.

Although we have depicted in FIG. 5A magnetic receiving sensors 43 of the types previously discussed it is herein emphasized that any type of sensor applicable to the generic node arrangements (but not necessarily backer 39) of FIGS. 3A and 3B are explicitly included herein. Thus we include all manner of energy or field-emitting sensor combinations-both those involving a transmitting and receiving sensor (as in FIG. 3A) or involving two receiving sensors (as in FIG. 3B).

We note also that spring portion 67 may itself be elastically deformable, for example in the Rh/20 plane, in order to best capture the cervical tissue 3' especially as it evolves in late labor into a lip or membrane 3' as shown in FIGS. 1A, 1B and 2E. The spring portion 67 may also incorporate additional features (not shown) such as molded-on silicone pads to ease tissue trauma.

Moving now to FIG. 5B we see a similar cervimeter device 22 to that seen in FIG. 5A. The main difference is that the FIG. 5B device has a spring portion 69 which is an elongated cantilever style spring which also generally follows the vaginal cavity wall. It is again emphasized that the spring 67/68/69 may take on any beneficial form including ones wherein the spring is wrapped on itself, crosses over itself or has markedly varying cross-section in different regions. Regions 67,68 and 69 need not necessarily be present or distinct and were shown simply as beneficial and desirable features. Moreover, the spring shape in FIG. 5B is illustrative only, and a variety of particular geometries could be employed.

Figure 6A:
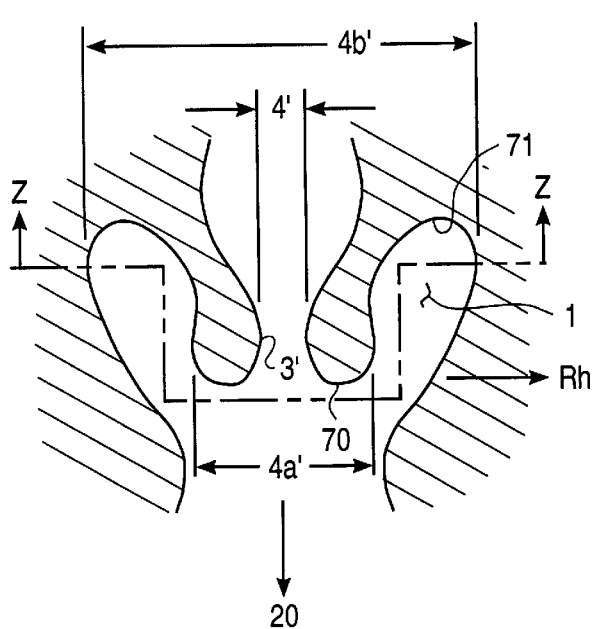
FIGS. 6A and 6B illustrate a sectional side view and a front view of the vaginal interior and cervix to be used in the later FIGS. 7A and 7B, 8A and 8B, and 9A and 9B. An early stage of dilatation is again indicated wherein the cervical canal remains generally tubular or cylindrical in shape.
Figure 6B:
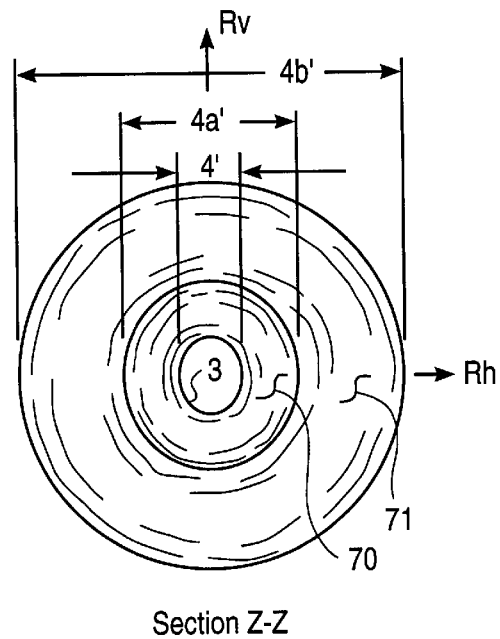

Moving now to FIG. 6A and 6B we simply see two views of the interior anatomy of the vaginal cavity and of the cervical structure within. It will be noted that in addition to familiar early cervical dilatation diameter 4' we also have labeled the corresponding outer diameter of the cervical os structure as 4a'. Further, we have indicated vaginal cavity diameter 4b' to be that taken approximately at the vaginal fornices. Section lines z-z in the sectional left hand side view (FIG. 6A) depict where the front view of FIG. 6B is taken from. A point on the front lip or surface of the cervical os is indicated as point 70 in both views. Another point, point 71 in the region of the vaginal fornice, is also indicated in both views. These related views will be utilized in the remaining FIGS. 7A and 7B, 8A and 8B, and 9A and 9B.

Figure 7A:
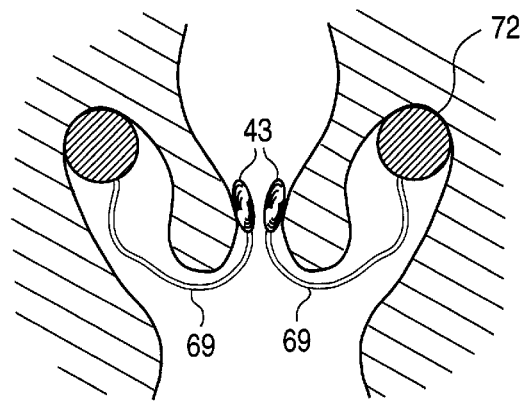
FIGS. 7A and 7B illustrate a ring-mounted or pessary-mounted orthogonal cervimeter having a nitinol spring mounted to each side of the ring, where each spring supports a position sensing means.
Figure 7B:
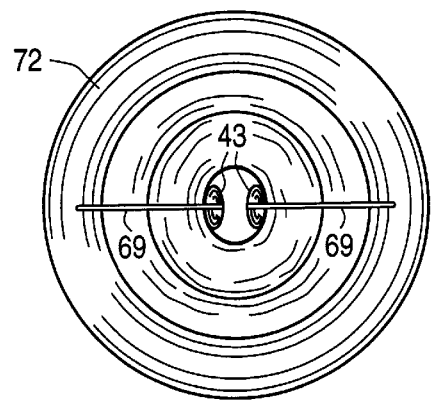

Moving now to the next figure, FIGS. 7A and 7B, which is based on the above FIGS. 6A and 6B anatomy, we see a first variation of a ring-mounted orthogonal cervimeter. The ring is indicated as structure 72 and may have the familiar expansive properties as earlier structure 39 such that it seats itself in the vaginal fornices (in the vicinity of points 71) and grows with them as the anatomy changes with dilatation. The ring may also, or alternatively, be pliable, soft, rubbery or inflatable so as both to maintain its seating as well as to reduce discomfort and patient irritation. Two generally orthogonal springs 69 are seen in both the side view (FIG. 7A) and the front view (FIG. 7B). The springs 69 are again shown as urging familiar position sensor means 43 against the interior diameter of the growing cervix 4'. It will be noted that springs 69 do not block the cervix from external access. Springs 69, in addition to having all of the material and fabrication possibilities previously cited as with relation to FIGS. 5A and 5B, are designed to bend such that sensors 43 may maintain positions representative of the desired cervical diameter (e.g. diameter 4') or other dimension to be monitored. As before, spring 69 may have variable cross-section and may consist of multiply oriented segments as opposed to a purely monotonic single section as shown. Nitinol, preferably in its superelastic form, is the preferred material for springs 69. The key attribute of the cervimeter of FIGS. 7A and 7B and of later FIGS. 8A and 8B and 9 A and 9D is that it has at least some orthogonal structural component lying parallel to axis 20 which allows for properly placed sensors 43 to be reached by a needed spring means 69. This is the same as saying the spring 69 and/or its supporting means isn't entirely contained in or parallel to a cervical diameter plane. It will immediately be recognized that ring structure 72 may also take a noncircular shape such as that of a familiar pessary device for example. Ring 72 also does not necessarily have to be a ring closed upon itself (unclosed not shown). Ring 72 does, however, provide for directly or indirectly supporting the springs 69. It will also be obvious that one might fabricate ring 72 and springs 69 out of the same material or that they may be all part of a single multisegment spring. At or near the point where each spring 69 meets sensor 43 one may also utilize a hinged or pivotable joint such that the sensor 43 may remain flat against the tissue being gripped regardless of the state of dilatation. We have already discussed the use of separate rubber or elastic spring regions or members near the sensor 43 in FIGS. 5A and 5B to also achieve this tracking and reorienting function as necessary.

Figure 8A:
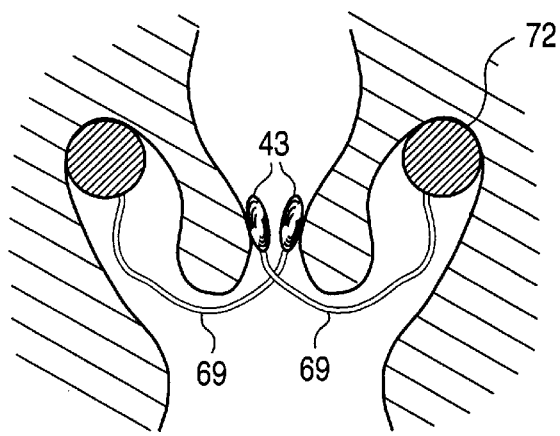
FIGS. 8A and 8B illustrate another ring-mounted orthogonal cervimeter having a nitinol spring mounted to each side of the ring, where overlapping springs each support a position sensing means.
Figure 8B:
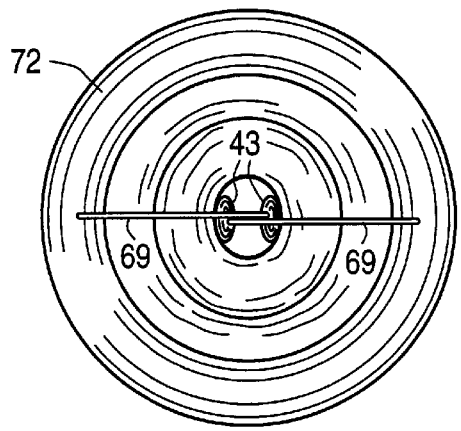

Moving now to the next figure, FIGS. 8A and 8B, which is also based on the above FIGS. 6A and 6B anatomy, we see a second variation of a ring-mounted orthogonal cervimeter. Ring 72, springs 69 and sensors 43 are again depicted. The significant difference herein relative to FIGS. 7A and 7B is that the springs are arranged to cross each other in a manner such that each spring is effectively tracking the opposite wall of the cervix. The key difference in this device is that the springs 69 unbend open rather than unbend closed.

Figure 9A:
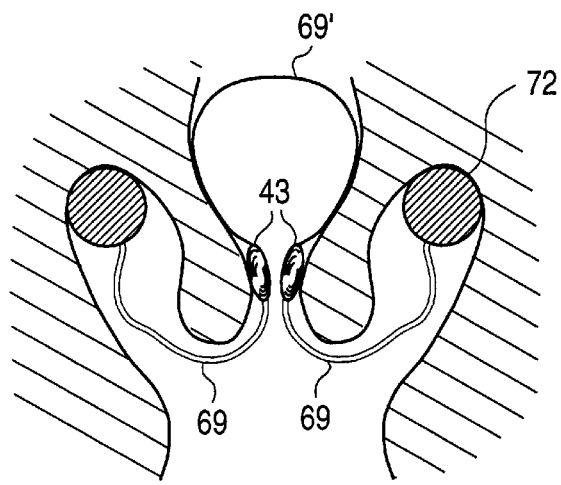
FIGS. 9A and 9B illustrate yet another ring-mounted orthogonal cervimeter having an additional spring component within the cervix.
Figure 9B:
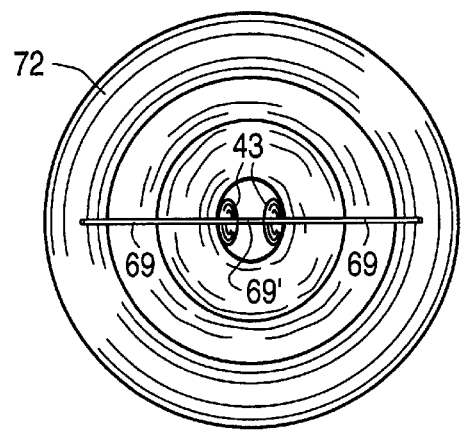

Moving finally now to FIGS. 9A and 9B we see a third variation of a ring-mounted orthogonal cervimeter. This device is similar to that of FIGS. 7A and 7B except that an additional spring component 69' shown in the cervix itself is also included. The additional spring 69' is shown as a loop attached to each sensor 43 location and extending into the cervix. Loop 69' may be a closed loop or an open loop. Its purpose is to further aid in locating the sensors 43 against the moving tissue of interest.

Many of the devices of the invention and of the various figures may be inserted easily in the cervix by first temporarily collapsing them. The collapsing action may be induced as by manual squeezing and may be maintained by placing the collapsed device in an internally slippery tube. The device may then be pushed out of the tube into the cervix and allowed to expand radially and/or longitudinally. Such tube delivery has been widely used to insert fetal scalp monitors and uterine pressure sensors wherein a tube of approximately 8 mm external diameter is utilized for this purpose. In this way such tube delivery is seen by the inventors as being convenient and familiar where possible. Insertion of the devices herein would likely require different tube diameters depending on the device.

Certain other of the devices, such as those of FIGS. 7 A and 7B, 8A and 8B, and 9A and 9B may be inserted as with a normal pessary device. In any event the devices would be sterilized so as to avoid infection.

Many of the devices of the invention may be elected to be self-contained, as powered by internal battery power. In such an approach the data representing the measurement may be transmitted via telemetry directly from the vaginally or cervically positioned device. An example of such a micro-miniaturized telemetry device is the STRAINLINK™ available from MicroStrain of Burlington, Vermont (Reference 40). A transmission frequency from 300 to 900 Mhz is selectable with that telemetry product.

Given that we can utilize a foam-containing or other pliable expandable structure such as 39 or 39' or 52 as a foundation for our cervimeter means, it becomes obvious that one might also utilize this already-present structure for purposes other than cevimetry but related to other cervical needs present during, or proximate in time to, a cervimetry session. As an example one might infuse portions of structure 39 or 39' with beneficial drugs to be delivered to the patient's cervical tissues. Alternatively, one might install a container of such a drug and a related dispensing mechanism within or attached to structure 39 or 39'. One could even use the cervimeter measurement data to control the administration of such a drug in a closed-loop system. Drugs that might be administered in this manner include, but are not limited to, antimicrobials, tocolytics, cervical ripening agents, and local anesthetics.

Expandable support structure 39 or 39' may also optionally either provide port access for other fetal and/or maternal instrumentation or may have integrated into it such additional instruments or probes. For example, such probes may include fetal scalp electrodes, intrauterine pressure transducers or blood oximeters. In the integrated approach, such a device may save one from having to remove or upset a cervimeter while installing such an added instrument or probe.

Although the foregoing invention has been described in some detail by way of illustration and example, for purposes of clarity of understanding, it will be obvious that certain changes and modifications may be practiced within the scope of the appended claims.

What is claimed is:

1. A cervimeter comprising:
    a loop element which is adapted to be securable to a cervix in a human female, wherein a peripheral length of the loop varies directly with a change in cervical size; and
    a gauge coupled to the loop element for measuring the change in loop dimension wherein the gauge is calibrated to show cervical dilation.

2. A cervimeter as in claim 1, further comprising a circumferentially expansible race which secures the loop to the cervix and permits the loop to expand and contract peripherally with the cervix.

3. A cervimeter as in claim 2, wherein the race is adapted to engage an interior wall of the cervix.

4. A cervimeter as in claim 2, wherein the race is adapted to engage an exterior wall of the cervix.

5. A cervimeter as in claim 2, wherein the race comprises a plurality of bearing elements having tissue anchors, which bearing elements may be distributed peripherally about the cervix.

6. A cervimeter as in claim 2, wherein the race comprises an expansible support structure which conforms to and expands with a surface the cervix.

7. A cervimeter as in claim 6, wherein the expansible support structure has a surface which conforms to the surface of the cervix, wherein the loop element is slidably captured between the support structure surface and the cervical surface.

8. A cervimeter as in claim 7, wherein the expansible support structure surface has an annular channel which receives the loop element.

9. A cervimeter as in claim 8, wherein the expansible support structure is an elastic body which is adapted to mount within the interior of the cervix or over the exterior of the cervix.

10. A cervimeter as in claim 9, wherein the expansible support structure comprises a foam cylinder or cup.

11. A cervimeter as in claim 2, wherein the race comprises a tubular ring which is adapted to extend substantially completely about the cervix, said tubular ring having tissue anchors for securing to the cervix.

12. A cervimeter as in claim 2, wherein the loop element is a compliant wire or tape, having one end fixed within the race and a free end, wherein the free end moves relative to the race as the cervical size changes.

13. A cervimeter as in claim 12, wherein the loop element is composed at least in part of a material which is superelastic at body temperature.

14. A cervimeter as in claim 2, wherein the gauge comprises an uptake tube which receives a free end of the loop element and which extends away from the race.

15. A cervimeter as in claim 14, wherein the gauge further comprises a sensor which detects and displays axial movement of the free end of the loop element through the uptake tube.

16. A cervimeter as in claim 14, wherein the gauge further comprises a visual scale which permits direct visual observation of the axial movement of the free end of the loop element through the uptake tube.

17. A cervimeter system comprising:
an expansible support structure having a surface which is adapted to conform to and expand with a circumference of 2 cervix; and
means for measuring changes in the size of the expansible support structure which result from changes in a cervical dimension and for correlating the measured change in size with cervical dilation.

18. A cervimeter as in claim 17, wherein the expansible support structure has a surface which is adapted to conform to a surface of the cervix.

19. A cervimeter as in claim 18, wherein the support structure is an elastic body which is adapted to mount within the interior of the cervix or over the exterior of the cervix.

20. A cervimeter as in claim 19, wherein the support structure comprises a foam cylinder or cup.

21. A cervimeter as in claim 17, wherein the measuring means comprises a loop element which is slidably received along the conformable surface of the expansible support structure.

22. A cervimeter as in claim 21, wherein the loop element is a compliant wire or tape, having one end fixed relative to the expansible support structure, and a free end, wherein the free end moves relative to the support structure as the cervical size changes.

23. A cervimeter as in claim 22, wherein the loop element is composed at least in part of a material which is superelastic material at body temperature.

24. A cervimeter as in claim 17, wherein the measuring means comprises at least a first measurement node and a second measurement node coupled to move with the conformable surface of the expansible support structure.

25. A cervimeter as in claim 24, wherein the first measurement node comprises a transmitter and the second measurement node comprises a receiver, further comprising circuitry coupled to the transmitter and receiver for determining the distance between the nodes.

26. A cervimeter as in claim 24, wherein both the first and second measurement nodes comprise at least one receiver, further comprising an external transmitter and circuitry for determining the distance between the nodes when the receivers are excited by the transmitter.

27. A cervimeter as in claim 24, wherein the measurement nodes are magnetic.

28. A cervimeter comprising:
a support structure which is adapted to engage at least one of the cervix or a portion of the vaginal wall proximate the cervix; and
at least two radially deployable wires supported by the expansive support structure, said wires each having a free distal end which is securable to a peripheral location on a cervix; and
a gauge coupled to the wires for measuring cervical size.

29. A cervimeter as in claim 28, wherein the support structure comprises a spring having at least two elements which engage inner peripheral surfaces of the cervix.

30. A cervimeter as in claim 29, wherein the measuring means is mounted on the spring elements and comprises at least a first measurement node and a second measurement node adapted to couple to the inner peripheral surfaces of the cervix.

31. A cervimeter as in claim 30, wherein the first measurement node comprises a transmitter mounted on one spring element and the second measurement node comprises a receiver mounted on the other spring element, further comprising circuitry coupled to the transmitter and receiver for determining the distance between the nodes.

32. A cervimeter as in claim 30, wherein both the first and second measurement nodes comprise at least one receiver mounted on each spring element, further comprising an external transmitter and circuitry for determining the distance between the nodes when the receivers are excited by the transmitter.

33. A cervimeter as in claim 28, wherein the support structure comprises a ring or pessary which is adapted to mount within the vaginal cavity or fornices.

34. A cervimeter as in claim 33, wherein the support structure further comprises a pair of spring elements adapted to extend from the ring into the cervix and which engage inner peripheral surfaces of the cervix.

35. A cervimeter as in claim 34, wherein the measuring means is mounted on the spring elements and comprises at least a first measurement node and a second measurement node adapted to couple to the inner peripheral surfaces of the cervix.

36. A cervimeter as in claim 34, wherein the first measurement node comprises a transmitter mounted on one spring element and the second measurement node comprises a receiver mounted on the other spring element, further comprising circuitry coupled to the transmitter and receiver for determining the distance between the nodes.

37. A cervimeter as in claim 34, wherein both the first and second measurement nodes comprise at least one receiver mounted on each spring element, further comprising an external transmitter and circuitry for determining the distance between the nodes when the receivers are excited by the transmitter.

38. A cervimeter comprising:
   at least two radially deployable wires, said wires each having distal end which is securable to a peripheral location on a cervix and a free proximal end; and
   a gauge coupled to the wires for measuring movement of the wires as an indication of changes in cervical size.

39. A cervimeter as in claim 41, further comprising an expansible support structure which is adapted to conform to the inner surface of a vaginal cavity, wherein the wires are deployed radially from the support structure.

40. A cervimeter as in claim 39, wherein the gauge is mounted on the support structure and comprises a sensor which detects radial movement of the wires.

41. A cervimeter comprising:
   an expansible coil which is insertable into a cervical os and which uncoils as the os dilates, and
   a gauge coupled to the coil for measuring cervical size.

42. A cervimeter as in claim 41, further comprising an expansible support structure which conforms the inner surface of a vaginal cavity, wherein the expansible coil is mounted on the expansible support structure.

43. A cervimeter as in claim 41, wherein the gauge is at least one strain gauge attached to the coil to measure the degree of uncoiling.

44. A method for detecting changes in the size of a cervix, said method comprising:
   securing a conformable structure to a surface of the cervix wherein the structure has a peripheral length which expands and contracts together with expansion and contraction of the cervix;
   measuring expansion and contraction of the peripheral length of the conformable structure, and correlating the measured change in length with cervical dilation.

45. A method as in claim 44, wherein the conformable structure comprises a loop element and wherein the measuring step comprises measuring uptake and release of the loop element.

46. A method as in claim 45, wherein the loop element is secured to a cervical surface in a race.

47. A method as in claim 46, wherein the race comprises a plurality of bearing elements which are anchored into the cervical surface.

48. A method as in claim 46, wherein the race comprises a circumferentially expansible tubular ring which is anchored into the cervix.

49. A method as in claim 46, wherein the race comprises an expansible support structure which is inserted into or over the cervical surface.

50. A method as in claim 44, wherein the conformable structure comprises a plurality of measurement nodes about its periphery and wherein the measuring step comprises detecting relative positions of at least one pair of the measurement nodes.

51. A method as in claim 50, wherein at least one measurement node is an energy flux or field transmitter, and at least one measurement node is an energy receiver, and the measuring step comprises determining changes in energy intensity or attenuation which result from changes in relative position.

52. A method as in claim 50, wherein at least two measurement nodes comprise magnetic sensors, and the measuring step comprises determining the relative positions of the magnetic sensors.

53. A method as in claim 44, wherein the conformable structure comprises a coil and the measuring step comprises detecting unwinding of the coil within the cervical os.

54. A method as in claim 53, further comprising directing current through the coil and detecting changes in the resulting magnetic field.

55. A method as in claim 53, wherein the unwinding of the coil is detected by measuring stress on the coil.

56. A cervimeter comprising:
   a support structure which engages at least one of the cervix or a portion of the vaginal wall proximate the cervix;
   an expansible coil mounted on the expansible support surface, which is insertable into a cervical Os and which uncoils as the os dilates, and
   a gauge coupled to the coil for measuring cervical size.

57. A cervimeter as in claim 56, wherein the support structure comprises a spring having at least two elements which engage inner peripheral surfaces of the cervix.

58. A cervimeter as in claim 57, wherein the measuring means is mounted on the spring elements and comprises at least a first measurement node and a second measurement node coupled to the inner peripheral surfaces of the cervix.

59. A cervimeter as in claim 58, wherein the first measurement node comprises a transmitter mounted on one spring element and the second measurement node comprises a receiver mounted on the other spring element, further comprising circuitry coupled to the transmitter and receiver for determining the distance between the nodes.

60. A cervimeter as in claim 58, wherein both the first and second measurement nodes comprise at least one receiver mounted on each spring element, further comprising an external transmitter and circuitry for determining the distance between the nodes when the receivers are excited by the transmitter.

61. A cervimeter as in claim 56, wherein the support structure comprises a ring or pessary which is mountable within the vaginal cavity or fornices.

62. A cervimeter as in claim 61, wherein the support structure further comprises a pair of spring elements extending from the ring into the cervix and which engage inner peripheral surfaces of the cervix.

63. A cervimeter as in claim 62, wherein the measuring means is mounted on the spring elements and comprises at least a first measurement node and a second measurement node coupled to the inner peripheral surfaces of the cervix.

64. A cervimeter as in claim 62, wherein the first measurement node comprises a transmitter mounted on one spring element and the second measurement node comprises a receiver mounted on the other spring element, further comprising circuitry coupled to the transmitter and receiver for determining the distance between the nodes.

65. A cervimeter as in claim 62, wherein both the first and second measurement nodes comprise at least one receiver mounted on each spring element, further comprising an external transmitter and circuitry for determining the distance between the nodes when the receivers are excited by the transmitter.

66. A cervimeter comprising:
   a support structure comprising a pair of diverging spring elements spring-biased to engage against the inner wall of the cervix; and
   means on the support structure for measuring changes in a cervical dimension.

67. A cervimeter as in claim 66, wherein the measuring means is mounted on the spring elements and comprises at least a first measurement node and a second measurement node adapted to couple to the inner peripheral surfaces of the cervix.

68. A cervimeter as in claim 67, wherein the first measurement node comprises a transmitter mounted on one spring element and the second measurement node comprises a receiver mounted on the other spring element, further comprising circuitry coupled to the transmitter and receiver for determining the distance between the nodes.

69. A cervimeter as in claim 67, wherein both the first and second measurement nodes comprise at least one receiver mounted on each spring element, further comprising an external transmitter and circuitry for determining the distance between the nodes when the receivers are excited by the transmitter.

70. A cervimeter as in claim 67, wherein the first and second measurement nodes are magnetic.

* * * * *